US008609660B2

(12) United States Patent
Trabanco-Suárez et al.

(10) Patent No.: US 8,609,660 B2
(45) Date of Patent: Dec. 17, 2013

(54) 4,7-DIHYDRO-PYRAZOLO[1,5-A]PYRAZIN-6-YLAMINE DERIVATIVES USEFUL AS INHIBITORS OF BETA-SECRETASE (BACE)

(75) Inventors: Andrés Avelino Trabanco-Suárez, Toledo (ES); Gary John Tresadern, Toledo (ES); Francisca Delgado-Jiménez, Toledo (ES)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 13/825,139

(22) PCT Filed: Sep. 20, 2011

(86) PCT No.: PCT/EP2011/066343
§ 371 (c)(1),
(2), (4) Date: Mar. 20, 2013

(87) PCT Pub. No.: WO2012/038438
PCT Pub. Date: Mar. 29, 2012

(65) Prior Publication Data
US 2013/0190318 A1   Jul. 25, 2013

(30) Foreign Application Priority Data

Sep. 22, 2010  (EP) .................................... 10178315
Mar. 11, 2011  (EP) .................................... 11157858

(51) Int. Cl.
*C07D 487/02* (2006.01)
(52) U.S. Cl.
USPC ........................................................ 514/249
(58) Field of Classification Search
None
See application file for complete search history.

(56) References Cited

FOREIGN PATENT DOCUMENTS

| WO | WO 2004/058176 | 7/2004 | | |
|----|----|----|----|----|
| WO | WO 2006/138265 | 12/2006 | | |
| WO | WO 2007/058583 | 5/2007 | | |
| WO | WO 2007058583 A2 * | 5/2007 | .......... | C07D 217/22 |
| WO | WO 2011/002409 | 1/2011 | | |
| WO | WO 2011002409 A1 * | 1/2011 | .......... | C07D 487/04 |

OTHER PUBLICATIONS

International Search Report for PCT/EP2011/066343 dated Apr. 11, 2011.
Written Opinion for PCT/EP2011/066343 dated Apr. 11, 2011.
Koike H et al., J Biochem. 1999, 126, 235-42.
Silvestri, R.: "Boom in the development of non-peptidic beta-secretase (BACE1) inhibitors for the treatment of Alzheimer's disease", Medicinal Research Reviews, New York. NY, US, vol. 29, No. 2, Mar. 1, 2009, pp. 295-338.

* cited by examiner

*Primary Examiner* — Dennis Heyer
*Assistant Examiner* — Daniel M Podgorski
(74) *Attorney, Agent, or Firm* — Yuriy P. Stercho

(57) ABSTRACT

The present invention relates to novel 4,7-dihydro-pyrazolo[1,5-a]pyrazin-6-yl-amine derivatives as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease or dementia associated with beta-amyloid.

7 Claims, No Drawings

4,7-DIHYDRO-PYRAZOLO[1,5-A]PYRAZIN-6-YLAMINE DERIVATIVES USEFUL AS INHIBITORS OF BETA-SECRETASE (BACE)

CROSS REFERENCE TO RELATED APPLICATIONS

This application is the national stage of PCT Application No. PCT/EP2011/066343, filed Sep. 20, 2011, which claims priority from European Patent Application No. 10178315.7, filed Sep. 22, 2010 and European Patent Application No. 11157858.9, filed Mar. 11, 2011, the entire disclosures of which are hereby incorporated in their entirety.

FIELD OF THE INVENTION

The present invention relates to novel 4,7-dihydro-pyrazolo[1,5-a]pyrazin-6-yl-amine derivatives as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease or dementia associated with beta-amyloid.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibillary tangles which are generated by hyperphosphorylation of tau protein and amyloid plaques which form by aggregation of beta-amyloid 1-42 (Abeta 1-42) peptide. Abeta 1-42 forms oligomers and then fibrils, and ultimately amyloid plaques. The oligomers and fibrils are believed to be especially neurotoxic and may cause most of the neurological damage associated with AD. Agents that prevent the formation of Abeta 1-42 have the potential to be disease-modifying agents for the treatment of AD. Abeta 1-42 is generated from the amyloid precursor protein (APP), comprised of 770 amino acids. The N-terminus of Abeta 1-42 is cleaved by beta-secretase (BACE), and then gamma-secretase cleaves the C-terminal end. In addition to Abeta 1-42, gamma-secretase also liberates Abeta 1-40 which is the predominant cleavage product as well as Abeta 1-38 and Abeta 1-43. These Abeta forms can also aggregate to form oligomers and fibrils. Thus, inhibitors of BACE would be expected to prevent the formation of Abeta 1-42 as well as Abeta 1-40, Abeta 1-38 and Abeta 1-43 and would be potential therapeutic agents in the treatment of AD.

SUMMARY OF THE INVENTION

The present invention is directed to a compound of Formula (I)

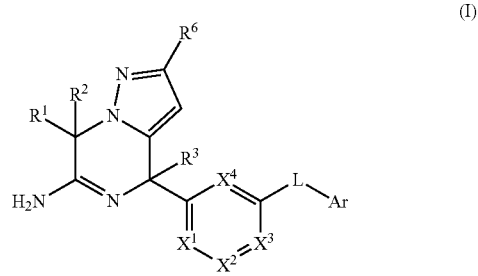

or a tautomer or a stereoisomeric form thereof, wherein
$R^1$ and $R^2$ are independently selected from the group consisting of hydrogen, fluoro, cyano, $C_{1-3}$alkyl, mono- and polyhalo-$C_{1-3}$alkyl, and $C_{3-6}$cycloalkyl; or
$R^1$ and $R^2$ taken together with the carbon atom to which they are attached may form a $C_{3-6}$cycloalkanediyl ring;
$R^3$ is selected from the group consisting of hydrogen, $C_{1-3}$alkyl, $C_{3-6}$cycloalkyl, mono- and polyhalo-$C_{1-3}$alkyl, homoaryl and heteroaryl;
$X^1, X^2, X^3, X^4$ are independently $C(R^4)$ or N, provided that no more than two thereof represent N; each $R^4$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;
L is a bond or —N($R^5$)CO—, wherein $R^5$ is hydrogen or $C_{1-3}$alkyl;
$R^6$ is hydrogen or trifluoromethyl;
Ar is homoaryl or heteroaryl;
homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl; and mono- and polyhalo-$C_{1-3}$alkyloxy;
heteroaryl is selected from the group consisting of pyridyl, pyrimidyl, pyrazyl, pyridazyl, furanyl, thienyl, pyrrolyl, pyrazolyl, imidazolyl, triazolyl, thiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl; and mono- and polyhalo-$C_{1-3}$alkyloxy; or
an addition salt or a solvate thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the beta-secretase enzyme, comprising administering to a subject in need thereof a therapeutically effective amount of any of the compounds or pharmaceutical compositions described above.

Further exemplifying the invention are methods of inhibiting the beta-secretase enzyme, comprising administering to a subject in need thereof a therapeutically effective amount of any of the compounds or pharmaceutical compositions described above.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described above.

Another example of the invention is any of the compounds described above for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I) as defined hereinbefore, and pharmaceutically acceptable salts and solvates thereof. The compounds of formula (I) are inhibitors of the beta-secretase enzyme (also known as beta-site cleaving enzyme, BACE, BACE1, Asp2 or memapsin 2), and are useful in the treatment of Alzheimer's disease, mild cognitive impairment, senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment of the present invention, $R^1$ and $R^2$ are independently selected from hydrogen and $C_{1-3}$alkyl;
$X^1$, $X^2$, $X^3$, $X^4$ are independently $C(R^4)$ wherein each $R^4$ is selected from hydrogen and halo;
L is a bond or —$N(R^5)CO$—, wherein $R^5$ is hydrogen;
Ar is homoaryl or heteroaryl;
homoaryl is phenyl or phenyl substituted with one or two substituents selected from the group consisting of halo, cyano, $C_{1-3}$alkyl, and $C_{1-3}$alkyloxy;
heteroaryl is selected from the group consisting of pyridyl, pyrimidyl, and pyrazyl, each optionally substituted with one or two substituents selected from the group consisting of halo, cyano, $C_{1-3}$alkyl, and $C_{1-3}$alkyloxy; or
an addition salt or a solvate thereof.
In another embodiment of the present invention, $R^1$ and $R^2$ are hydrogen;
$X^1$, $X^2$, $X^3$, $X^4$ are CH;
L is a bond or —$N(R^5)CO$—, wherein $R^5$ is hydrogen;
Ar is homoaryl or heteroaryl;
homoaryl is phenyl substituted with chloro;
heteroaryl is selected from the group consisting of pyridyl and pyrimidyl, each optionally substituted with one or two substituents selected from the group consisting of chloro, fluoro, cyano, methyl, and methoxy; or
an addition salt or a solvate thereof.
In another embodiment, the carbon atom substituted with $R^3$ has the R-configuration.
In another embodiment of the present invention, $R^1$ and $R^2$ are hydrogen;
$X^1$ is CH or CF, and $X^2$, $X^3$, $X^4$ are CH;
L is —$N(R^5)CO$—, wherein $R^5$ is hydrogen;
Ar is pyridinyl substituted with one or two halo atoms, or pyrazinyl substituted with methoxy; or
an addition salt or a solvate thereof.

DEFINITIONS

"Halo" shall denote fluoro, chloro and bromo; "$C_{1-3}$alkyl" shall denote a straight or branched saturated alkyl group having 1, 2 or 3 carbon atoms, e.g. methyl, ethyl, 1-propyl and 2-propyl; "$C_{1-3}$alkyloxy" shall denote an ether radical wherein $C_{1-3}$alkyl is as defined before; "mono- and polyhalo$C_{1-3}$alkyl" shall denote $C_{1-3}$alkyl as defined before, substituted with 1, 2 3 or where possible with more halo atoms as denied before; "mono- and polyhalo$C_{1-3}$alkyloxy" shall denote an ether radical wherein mono- and polyhalo$C_{1-3}$alkyl is as defined before;
"$C_{3-6}$cycloalkyl" shall denote cyclopropyl, cyclobutyl, cyclopentyl and cyclohexyl;
"$C_{3-6}$cycloalkanediyl" shall denote a bivalent radical such as cyclopropanediyl, cyclobutanediyl, cyclopentanediyl and cyclohexanediyl.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds according to formula (I) and the addition salts, hydrates and solvates thereof may contain one or more centers of chirality and exist as stereoisomeric forms.

The term "stereoisomeric forms" as used hereinbefore or hereinafter defines all the possible stereoisomeric forms which the compounds according to formula (I) and their addition salts may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms according to formula (I) and their salts, solvates, substantially free, i.e. associated with less than 10%, preferably less than 5%, in particular less than 2% and most preferably less than 1% of the other isomers.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The chemical names of the compounds of the present invention were generated according to the nomenclature rules agreed upon by the Chemical Abstracts Service. The compounds according to formula (I) may also exist in their tautomeric form. Such forms although not explicitly indicated in the above formula are intended to be included within the scope of the present invention.

A. Preparation of the Final Compounds

Experimental Procedure 1

The final compounds according to Formula (I), can be prepared by reacting an intermediate compound of Formula (II) with an appropriate source of ammonia such as, for example, ammonium chloride or aqueous ammonia, according to reaction scheme (1), a reaction that is performed in a suitable reaction-inert solvent, such as, for example, water or methanol, under thermal conditions such as, for example, heating the reaction mixture at 60° C., for example for 6 hours. In reaction scheme (1), all variables are defined as in Formula (I).

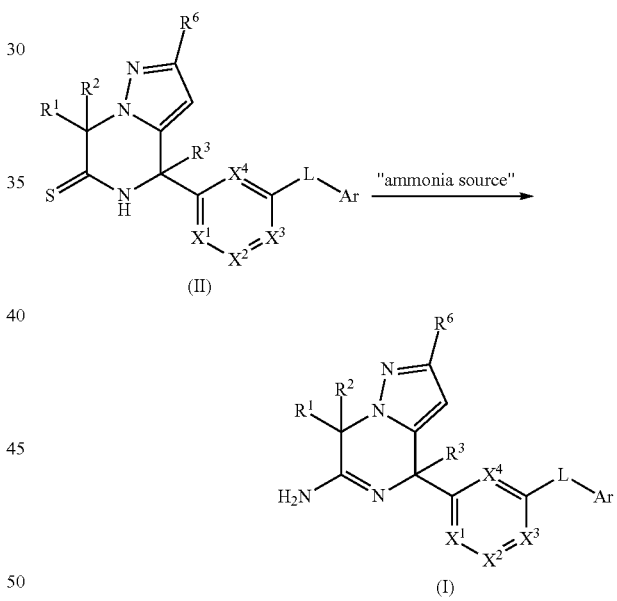

Experimental Procedure 2

The final compounds according to Formula (I-a) wherein L is —N(R$^5$)CO—, can be prepared by reacting an intermediate compound of Formula (III-a) with an intermediate of Formula (IV) according to reaction scheme (2), a reaction that is performed in a suitable reaction-inert solvent, such as, for example, N,N-dimethyl-formamide, in the presence of a suitable base, such as, for example, K$_3$PO$_4$, a copper catalyst such as, for example, CuI and a diamine such as for example (1R,2R)-(−)-1,2-diaminocyclohexane, under thermal conditions such as, for example, heating the reaction mixture at 180° C., for example for 135 minutes under microwave irradiation. In reaction scheme (2), all variables are defined as in Formula (I) and W is halo.

Reaction Scheme 2

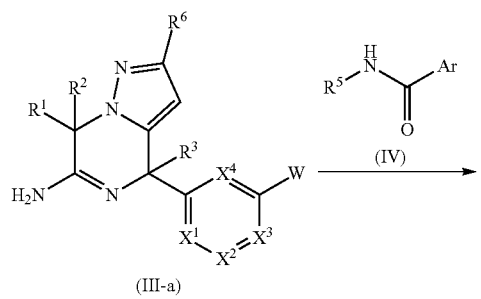

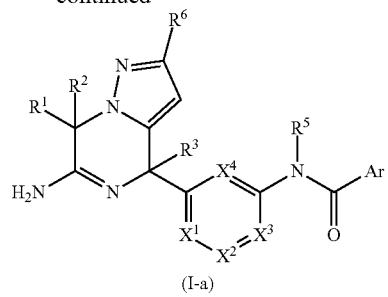

Experimental Procedure 3

Additionally, the final compounds according to Formula (I-a), can be prepared by reacting an intermediate compound of Formula (III-b) with an intermediate of Formula (V) according to reaction scheme (3), a reaction that is performed in a suitable reaction-inert solvent, such as, for example, dichloromethane, in the presence of a suitable base, such as, for example, triethylamine, in the presence of a condensation agent such as for example O-(7-azabenzotriazol-1-yl)-N,N,N',N'-tetramethyluronium hexafluorophosphate [HATU, CAS 148893-10-1], under thermal conditions such as, for example, heating the reaction mixture at 25° C., for example for 2 hours. In reaction scheme (3), all variables are defined as in Formula (I).

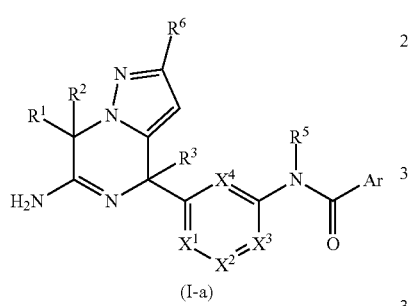

Experimental Procedure 4

Additionally, the final compounds according to Formula (I-a), can be prepared by reacting an intermediate compound of Formula (III-b) with an intermediate of Formula (VI) according to reaction scheme (4), a reaction that is performed in a suitable reaction-inert solvent, such as, for example, dichloromethane, in the presence of a suitable base, such as, for example, pyridine, under thermal conditions such as, for example, heating the reaction mixture at 25° C., for example for 2 hours. In reaction scheme (4), all variables are defined as in Formula (I) and Y is halo.

Reaction Scheme 4

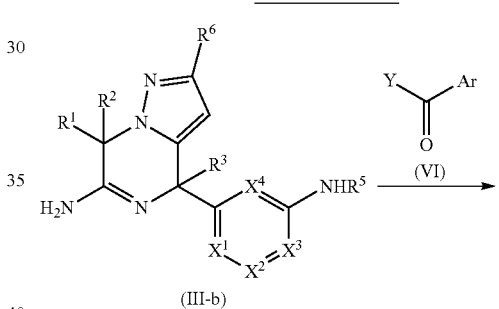

Experimental Procedure 5

The final compounds according to Formula (I-b) wherein L is a bond, can be prepared by reacting an intermediate compound of Formula (III-a) with an intermediate of Formula (VII) according to reaction scheme (5), a reaction that is performed in a suitable reaction-inert solvent, such as, for example, mixtures of inert solvents such as, for example, 1,4-dioxane/ethanol, in the presence of a suitable base, such as, for example, aqueous $K_3CO_3$, a Pd-complex catalyst such as, for example, tetrakis(triphenylphosphine)palladium (0) [CAS 14221-01-3] under thermal conditions such as, for example, heating the reaction mixture at 80° C., for example for 20 hours or for example, heating the reaction mixture at 150° C., for 10 minutes to 30 minutes under microwave irradiation. In reaction scheme (5), all variables are defined as

Reaction Scheme 3

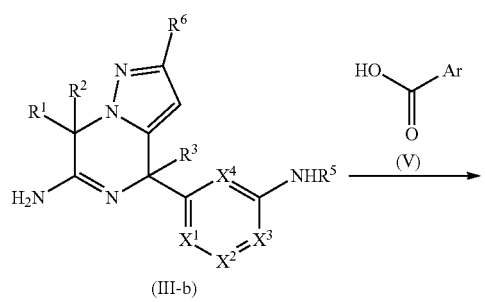

in Formula (I) and W is, halo. $R^7$ and $R^8$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

Reaction Scheme 5

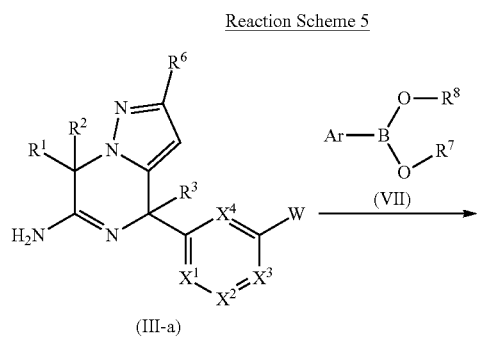

(III-a)

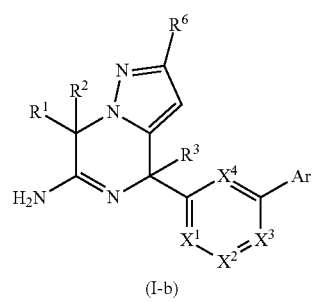

(I-b)

A number of intermediates and starting materials in the foregoing preparations are known compounds which may be prepared according to art-known methodologies of preparing said or similar compounds and some intermediates are new. A number of such preparation methods will be described hereinafter in more detail.

B. Preparation of the Intermediate Compounds

Experimental Procedure 6

The intermediates according to Formula (II) can be prepared by reacting an intermediate compound of Formula (VIII) with a suitable sulphur donating reagent for the synthesis of thioamides such as, for example, phosphorous pentasulfide or 2,4-bis-(4-methoxyphenyl)-1,3-dithia-2,4-diphosphetane 2,4-disulfide [Lawesson's reagent, CAS 19172-47-5] according to reaction scheme (6), a reaction that is performed in a reaction inert solvent, such as for example, tetrahydrofuran or toluene, in the presence of a suitable base such as, for example, pyridine, under thermal conditions such as, for example, heating the reaction mixture at 90° C., for example for 18 hours. In reaction scheme (6), all variables are defined as in Formula (I).

Reaction Scheme 6

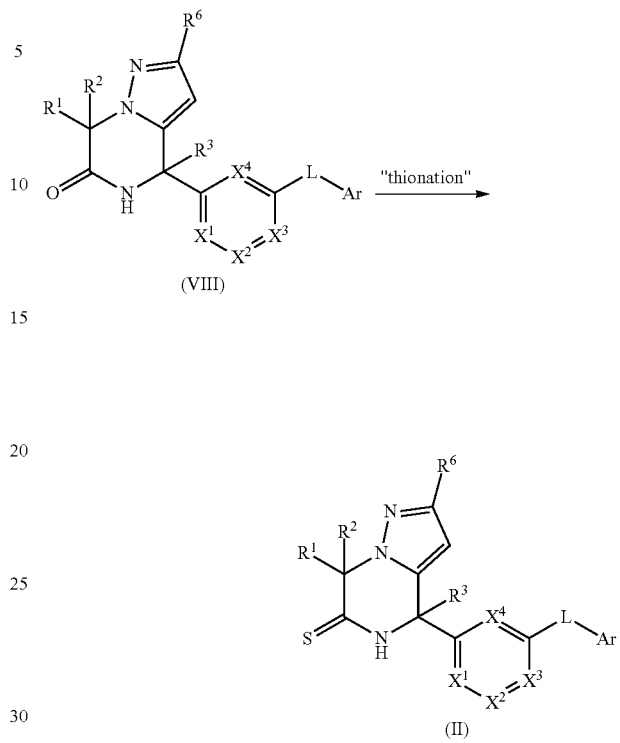

Experimental Procedure 7

The intermediates according to Formula (VIII), where L is a bond, can be prepared by reacting an intermediate compound of Formula (IX-a) with an intermediate of Formula (VII) according to reaction scheme (7), a reaction that is performed in a suitable mixture of inert solvents such as, for example, 1,4-dioxane/water, in the presence of a suitable base, such as, for example, aqueous $Na_2CO_3$, a Pd-complex catalyst such as, for example, tetrakis(triphenylphosphine) palladium (0) [CAS 14221-01-3] under thermal conditions such as, for example, heating the reaction mixture at 80° C., for example for 20 hours or for example, heating the reaction mixture at 150° C., for example for 15 minutes under microwave irradiation. In reaction scheme (7), all variables are defined as in Formula (I) and W is halo. $R^7$ and $R^8$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

Reaction Scheme 7

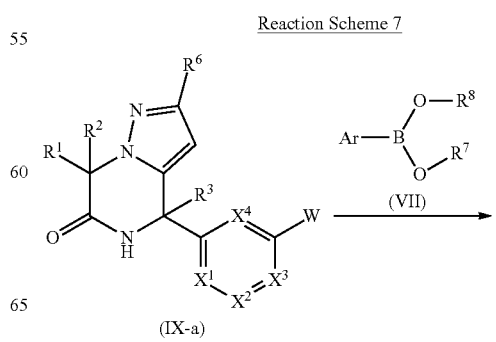

(IX-a)

-continued

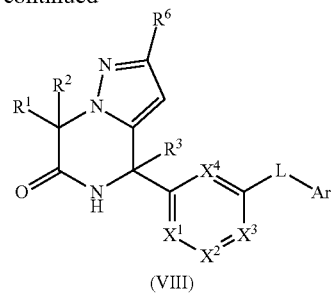

(VIII)

Experimental Procedure 8

The intermediates according to Formula (III-b) can be prepared from the corresponding intermediate compounds of Formula (III-a) following art-known Buchwald-Hartwig type coupling procedures according to reaction scheme (8). Said coupling may be conducted by treatment of intermediate compounds of Formula (III-a) with an intermediate of Formula (X) in a suitable reaction-inert solvent, such as, for example, ethanol or mixtures of inert solvents such as, for example, ethanol or mixtures of inert solvents such as, for example, 1,2-dimethoxyethane/water/ethanol, in the presence of a suitable base, such as, for example, aqueous $K_3PO_4$ or $Cs_2CO_3$, a Pd-complex catalyst such as, for example, [1,1'-bis(diphenylphosphino)ferrocene]-dichloropalladium(II) [CAS 72287-26-4] or trans-bis(dicyclohexylamine)palladium diacetate [DAPCy, CAS 628339-96-8] under thermal conditions such as, for example, heating the reaction mixture at 80° C., for example for 20 hours or for example, heating the reaction mixture at 130° C., for example for 10 minutes under microwave irradiation. In reaction scheme (8), all variables are defined as in Formula (I) and W is halo. $R^5$ is hydrogen or $C_{1-3}$alkyl.

Reaction Scheme 8

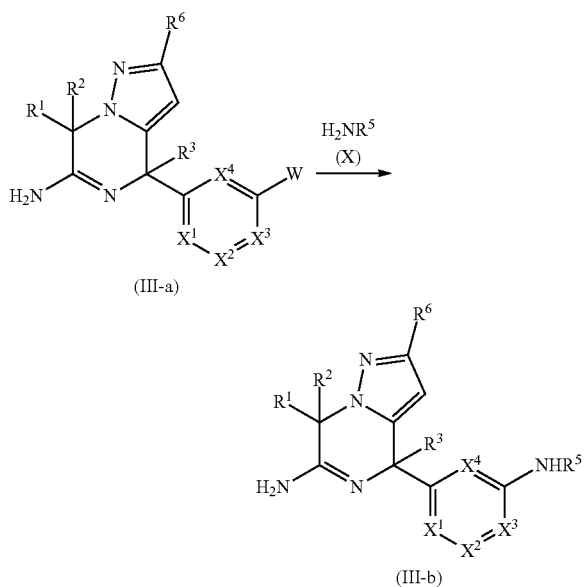

Experimental Procedure 9

Additionally, the intermediates according to Formula (III-b) wherein $R^5$ is hydrogen, can be prepared from the corresponding intermediates of Formula (III-c) following art-known nitro-to-amino reduction procedures according to reaction scheme (9). Said reduction may conveniently be conducted following art-known catalytic hydrogenation procedures. For example, said reduction may be carried out by stirring the reactants under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture. Undesired further hydrogenation of certain functional groups in the reactants and the reaction products may be prevented by the addition of a catalyst poison such as, for example, thiophene and the like, to the reaction mixture. In reaction scheme (9), all variables are defined as in Formula (I).

Reaction Scheme 9

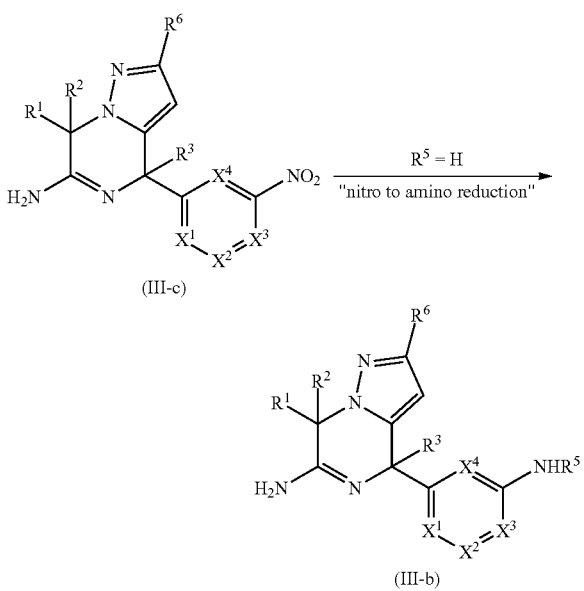

Experimental Procedure 10

The intermediate compounds of Formula (III-a) and (III-c) can generally be prepared following the reaction steps shown in the reaction schemes (10), (11), (12), and (13) below.

The amidine derivatives of Formula (III-a) and (III-c) in reaction scheme (10) may be conveniently prepared from the corresponding thioamide derivatives of Formula (XI-a) and (XI-c) following art-known thioamide-to-amidine conversion procedures (reaction step A). Said conversion may conveniently be conducted by treatment of intermediate compounds of Formula (XI-a) and (XI-c) with an ammonia source such as, for example, ammonium chloride or aqueous ammonia, in a suitable reaction-inert solvent such as, for example, water or methanol and the like, under thermal conditions such as, for example, heating the reaction mixture at 60° C., for example for 6 hours.

The thioamide derivatives of Formula (XI-a) and (XI-c) in reaction scheme (10) can be prepared from amide derivatives of Formula (IX-a) and (IX-c) following art-known thionation procedures (reaction step B). Said conversion may conveniently be conducted by treatment of intermediate compounds of Formula (IX-a) and (IX-c) with a thionation agent such as, for example, phosphorous pentasulfide or 2,4-bis-(4- methoxy-phenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, under thermal conditions such as, for example, heating the reaction mixture at 50° C., for example for 50 minutes.

The amide derivatives of Formula (IX-a) and (IX-c) in reaction scheme (10) can be prepared from the corresponding intermediate compounds of Formula (XII-a) and (XII-c) following art-known cyclization procedures (reaction step C). Said cyclization may conveniently be conducted by treatment of intermediate compounds of Formula (XII-a) and (XII-c) with a suitable base, such as sodium hydride, in a suitable reaction inert solvent, such as for example tetrahydrofuran and the like, at −80° C. to 100° C., preferably −15° C. to 25° C. for 30 minutes to 100 hours, preferably 1 hour to 24 hours.

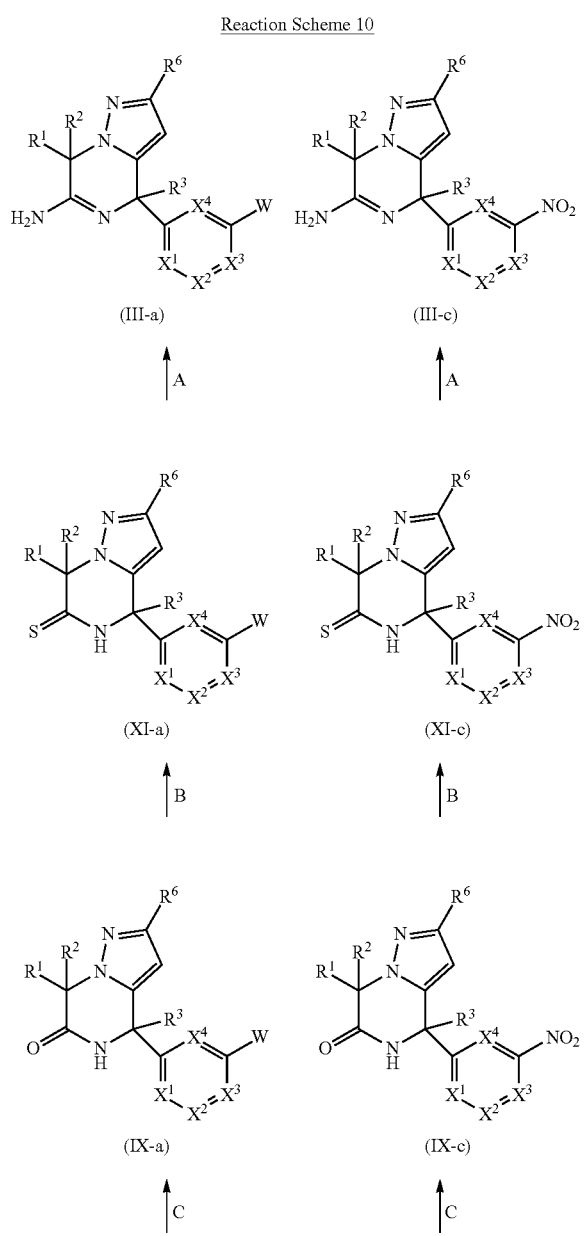

Reaction Scheme 10

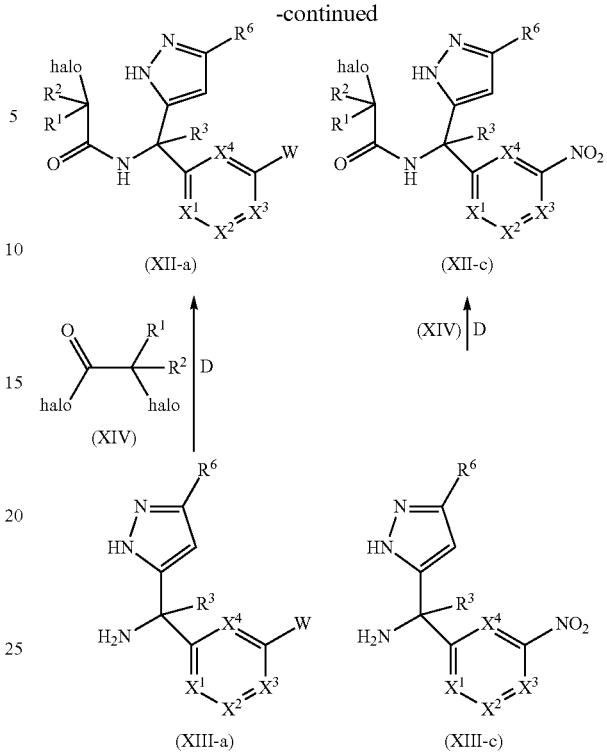

A: thioamide-to-amidine conversion
B: amide-to-thioamide conversion (thionation)
C: Cyclization
D: N-acylation The intermediate compounds of Formula (XII-a) and (XII-c) in the above reaction scheme (10) can be prepared from the corresponding intermediate compounds of Formula (XIII-a) and (XIII-c) following art-known N-acylation procedures (reaction step D). Said N-acylation may conveniently be conducted by treatment of the intermediate compounds of Formula (XIII-a) and (XIII-c) with an intermediate compound of Formula (XIV) in the presence of a base, such as sodium bicarbonate, or a mixture of bases such as sodium bicarbonate/N,N-diisopropylethylmine, in a suitable reaction inert solvent, such as for example ethanol or mixtures of inert solvents such as, for example, ethanol/dichloromethane, at −80° C. to 100° C., preferably −15° C. to 25° C. for 30 minutes to 100 hours, preferably 1 hour to 24 hours.

The intermediates according to Formula (XIII-a) and (XIII-c) in reaction scheme (11) can be prepared from the corresponding intermediate compounds of Formula (XV-a) and (XV-c), wherein $Z^1$ is a suitable protecting group of the pyrazol system, such as, for example, the dimethylsulfamoyl group, and $Z^2$ is a suitable protecting group of amines such as, for example, the tert-butanesulfinyl group, following art-known N-deprotection procedures (reaction step E). Said N-deprotection may conveniently be conducted by treatment of the corresponding intermediate compounds of Formula (XV-a) and (XV-c) with a suitable acidic agent such as, for example, hydrochloric acid, in a suitable inert solvent such as, for example, 1,4-dioxane, at a moderately high temperature such as, for example, 25° C., for example for 1 hour.

The intermediates according to Formula (XV-a) and (XV-c) in reaction scheme (11) can be prepared by reacting the intermediate compounds of Formula (XVII-a) and (XVII-c) following art-known imine to alkylamine conversion procedures (reaction step F). Said conversion may conveniently be conducted by treatment of the corresponding intermediate compounds of Formula (XVII-a) and (XVII-c) with an intermediate compound of Formula (XVI) wherein Y is halo, in a suitable reaction-inert solvent, such as, for example, tetrahydrofuran, at low temperature such as, for example, 0° C., for example for 2 hours.

Reaction Scheme 11

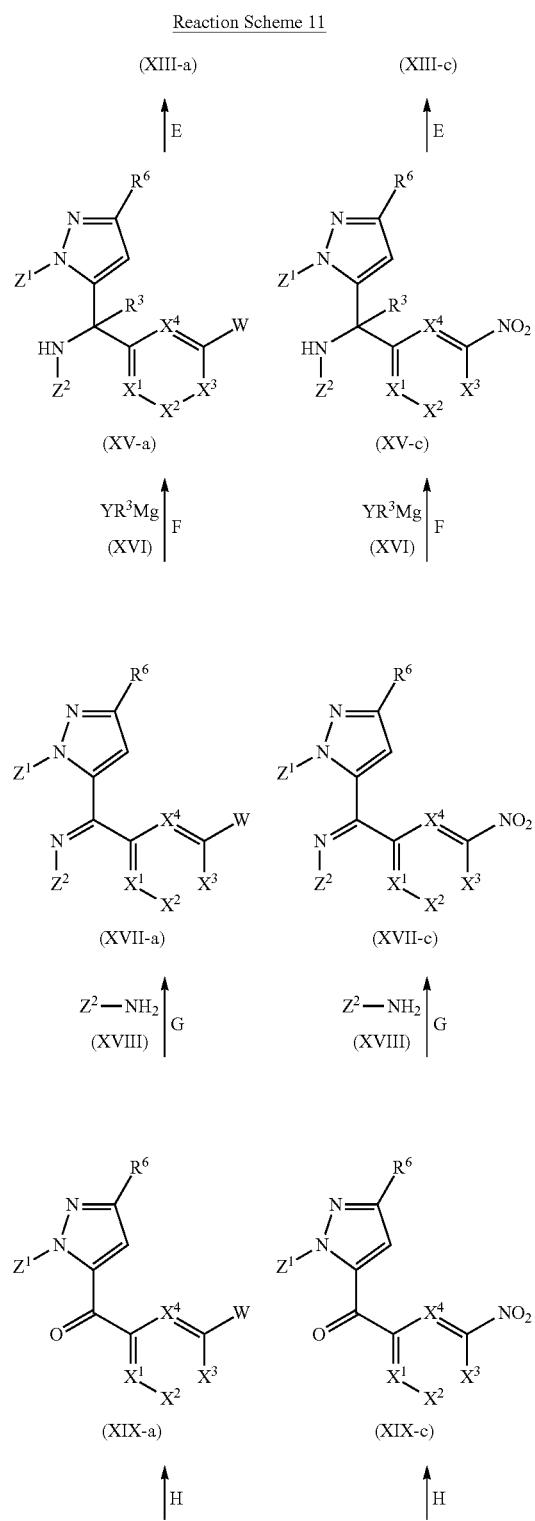

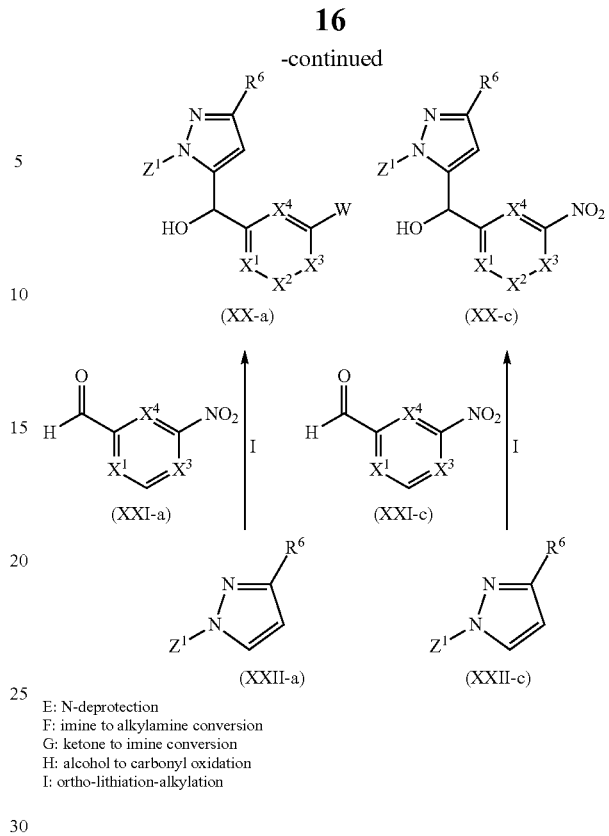

E: N-deprotection
F: imine to alkylamine conversion
G: ketone to imine conversion
H: alcohol to carbonyl oxidation
I: ortho-lithiation-alkylation The intermediates according to Formula (XVII-a) and (XVII-c) in the above reaction scheme (11) can be prepared by reacting the intermediate compounds of Formula (XIX-a) and (XIX-c) following art-known ketone to imine conversion procedures (reaction step G). Said conversion may conveniently be conducted by treatment of the corresponding intermediate compounds of Formula (XIX-a) and (XIX-c) with an intermediate compound of Formula (XVIII), wherein $Z^2$ is an alkylsulfinyl group such as, for example, the tert-butanesulfinyl group, in the presence of a suitable Lewis acid catalyst, such as titanium(IV)isopropoxide, in a suitable reaction-inert solvent, such as, for example, toluene, under thermal conditions such as, for example, heating the reaction mixture at 110° C., for example for 24 hours.

The intermediates according to Formula (XIX-a) and (XIX-c) in the above reaction scheme (11) can be prepared by reacting the intermediate compounds of Formula (XX-a) and (XX-c) following art-known alcohol to carbonyl oxidation procedures (reaction step H). Said oxidation may conveniently be conducted by treatment of the corresponding intermediate compounds of Formula (XX-a) and (XX-c) with an oxidant agent such as, for example, the Dess-Martin periodinane [CAS: 87413-09-0], in a suitable reaction-inert solvent, such as, for example, dichloromethane, at low temperature such as, for example, 0° C., for example for 10 minutes and then at a moderately high temperature such as, for example, 25° C., for example for 1 hour.

The intermediates according to Formula (XX-a) and (XX-c) in the above reaction scheme (11) can be prepared by reacting the intermediate compounds of Formula (XXII-a) and (XXII-c) following art-known ortho-lithiation-alkylation procedures (reaction step I). Said conversion may conveniently be conducted by treatment of the corresponding intermediate compounds of Formula (XXII-a) and (XXII-c) with a suitable organolithium reagent such as, for example, n-butyl lithium, in a suitable reaction-inert solvent, such as, for example, tetrahydrofuran, at low temperature such as, for example, −78° C., for example for 45 minutes followed by treatment with intermediate compounds of Formula (XXI-a) and (XXI-c), at low temperature such, as for example, −78° C., for example for 45 minutes.

The intermediates compounds of Formula (XXII-a) and (XXII-c), wherein $Z^1$ is a suitable protecting group of the pyrazol system, such as, for example, the dimethylsulfamoyl group, can generally be prepared following art-known N-protecting type procedures described in literature.

Reaction Scheme 12

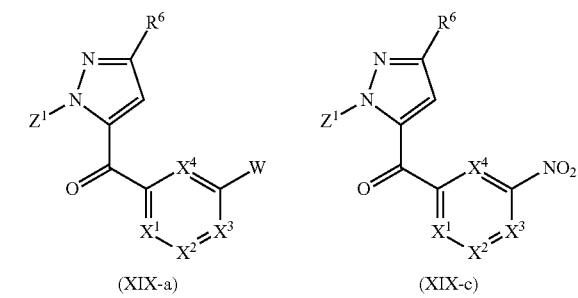

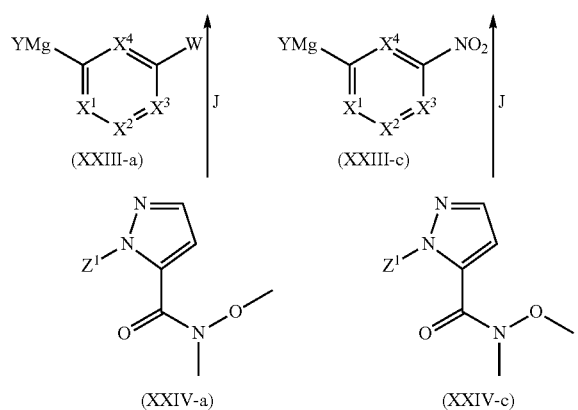

J: Weinreb amide to ketone conversion
K: Weinreb amide formation

Additionally, the intermediates according to Formula (XIX-a) and (XIX-c), wherein $R^6$ is hydrogen, in the above reaction scheme (12) can be prepared by reacting the intermediate compounds of Formula (XXIV-a) and (XXIV-c) following art-known Weinreb amide to ketone conversion procedures (reaction step J). Said conversion may conveniently be conducted by treatment of the corresponding intermediate compounds of Formula (XXIV-a) and (XXIV-c) with intermediate compounds of Formula (XXIII-a) and (XXIII-c) wherein Y is halo, in a suitable reaction-inert solvent, such as, for example, tetrahydrofuran, at low temperature such as, for example, −78° C., for example for 1 hour and then at a moderately high temperature such as, for example, 25° C., for example for 5 hours.

The intermediates according to Formula (XXIV-a) and (XXIV-c) in the above reaction scheme (12) can be prepared by reacting the intermediate compounds of Formula (XXV-a) and (XXV-c) following art-known Weinreb amide formation procedures (reaction step K). Said conversion may conveniently be conducted by treatment of the corresponding intermediate compounds of Formula (XXV-a) and (XXV-c) with N,O-dimethylhydroxylamine in the presence of a suitable base, such as, for example, isopropylmagnesium chloride, in a suitable reaction-inert solvent, such as, for example, dichloromethane, at low temperature such as, for example, −78° C., for example for 1 hour and then at a moderately high temperature such as, for example, 25° C., for example for 24 hours.

The intermediates compounds of Formula (XXV-a) and (XXV-c) wherein $Z^1$ is a suitable protecting group of the pyrazol system, such as, for example, the dimethylsulfamoyl group, are commercially available.

Additionally, the intermediates according to Formula (XIII-a) and (XIII-c), wherein $R^6$ is hydrogen, in the reaction scheme (13) can be prepared from the corresponding intermediate compounds of Formula (XXVI-a) and (XXVI-c), wherein $Z^3$ is a protecting group of amines such as, for example, the tert-butoxycarbonyl group (reaction step E), following art-known N-deprotection procedures such as the ones described in the reaction scheme (11) (reaction step E).

The intermediates according to Formula (XXVI-a) and (XXVI-c) in the reaction scheme (13) can be prepared by reacting the intermediate compounds of Formula (XXVII-a) and (XXVII-c) following art-known pyrazol ring formation procedures (reaction step L). Said pyrazol ring formation may conveniently be conducted by treatment of the corresponding intermediate compounds of Formula (XXVII-a) and (XXVII-c) in a suitable inert solvent such as, for example, ethanol, in the presence of hydrazine, at a moderately high temperature such as, for example, 25° C., for example for 1 hour.

The intermediates according to Formula (XXVII-a) and (XXVII-c) in the reaction scheme (13) can be prepared by reacting the intermediate compounds of Formula (XXVIII-a) and (XXVIII-c) following art-known alcohol to carbonyl oxidation procedures such as the ones described in the reaction scheme (11) (reaction step H).

Reaction Scheme 13

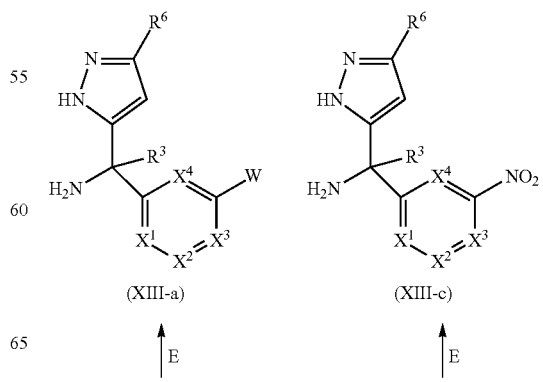

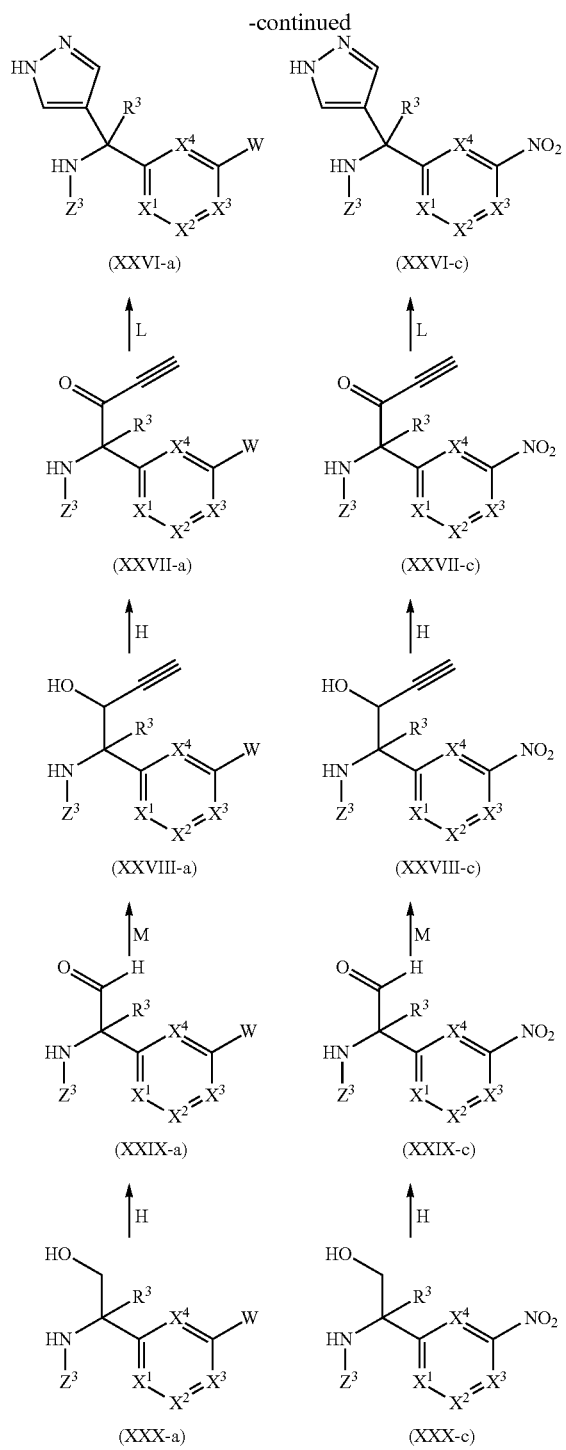

E: N-deprotection
L: pyrazol ring formation
H: alcohol to carbonyl oxidation
M: aldehyde to hydroxyalkynyl conversion The intermediates according to Formula (XXVIII-a) and (XXVIII-c) in the above reaction scheme (13) can be prepared by reacting the intermediate compounds of Formula (XXIX-a) and (XXIX-c) following art-known aldehyde to hydroxyalkynyl conversion procedures (reaction step M). Said conversion may conveniently be conducted by treatment of the corresponding intermediate compounds of Formula (XXIX-a) and (XXIX-c) with a suitable magnesium reagent such as, for example, ethynylmagnesium bromide, in a suitable reaction-inert solvent, such as, for example, tetrahydrofuran, at low temperature such as, for example, 0° C., for example for 10 minutes and then at a moderately high temperature such as, for example, 25° C., for example for 30 minutes.

The intermediates according to Formula (XXIX-a) and (XXIX-c) in the above reaction scheme (13) can be prepared by reacting the intermediate compounds of Formula (XXX-a) and (XXX-c) following art-known alcohol to carbonyl oxidation procedures such as the ones described in the reaction scheme (11) (reaction step H).

The intermediates compounds of Formula (XXX-a) and (XXX-c), wherein $Z^3$ is a protecting group of amines such as, for example, the tert-butoxycarbonyl group, can generally be prepared following art-known Strecker type procedures described in literature.

Pharmaceutical Compositions

The present invention also provides compositions for preventing or treating diseases in which inhibition of beta-secretase is beneficial, such as Alzheimer's disease (AD), mild cognitive impairment, senility, dementia, dementia with Lewy bodies, Down's syndrome, dementia associated with stroke, dementia associated with Parkinson's disease and dementia associated with beta-amyloid. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The following examples are intended to illustrate but not to limit the scope of the present invention.

Experimental Part

Hereinafter, "m.p." means melting point, "aq." means aqueous, "r.m." means reaction mixture, "r.t." means room temperature, 'DIPEA' means diisopropylethylamine, 'DIPE' means diisopropylether, Et$_2$O means diethyl ether, 'THF' means tetrahydrofuran, 'DMF' means dimethylformamide, 'DCM' means dichloromethane, 'AcOEt' means ethylacetate, 'AcOH' means acetic acid, 'MeOH' means methanol, 'EtOH' means ethanol, 'rac' means racemic, 'sat.' means saturated, 'SFC' means supercritical fluid chromatography, 'SFC-MS' means supercritical fluid chromatography/mass spectrometry, 'LCMS' means liquid chromatography/mass spectrometry, 'HPLC' means high-performance liquid chromatography, "DMTMM" means 4-(4,6-dimethoxy-1,3,5-triazin-2-yl)-4-methylmorpholinium chloride, "HATU" means O-(7-azabenzotriazol-1-yl)-N,N,N',N'-tetramethyluronium hexafluorophosphate.

A. Preparation of the Intermediates

Example A1

Preparation of intermediate 1:
rac-2-amino-2-(3-bromophenyl)-propanenitrile

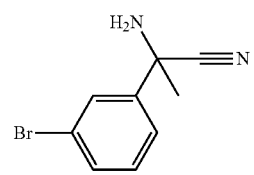

Trimethylsilylcyanide (20 g, 200 mmol) was added to a stirred solution of 3-bromoacetophenone (20 g, 100 mmol) and NH$_4$Cl (11 g, 200 mmol) in NH$_3$/MeOH (400 mL). The mixture was stirred at room temperature for 4 days. Then the solvent was evaporated in vacuo and the residue was taken up in AcOEt (100 mL). The solid was filtered off and the filtrate was evaporated in vacuo to yield rac-2-amino-2-(3-bromophenyl)-propionitrile (20 g, 86% yield) which was used in the next step without further purification.

Example A2

Preparation of intermediate 2: rac-methyl 2-amino-2-(3-bromophenyl)propanoate

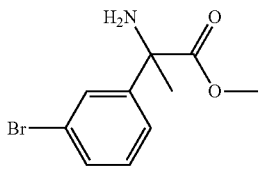

rac-2-Amino-2-(3-bromo-phenyl)-propionitrile (20 g, 88.9 mmol) was dissolved in HCl/MeOH (500 mL) and the mixture was refluxed for 4 days. After cooling to room temperature, AcOEt (100 mL) and water (100 mL) were added and the mixture was extracted with AcOEt (2×100 mL). The combined aqueous layers were basified with aqueous ammonia solution until pH 8 and extracted with AcOEt (5×100 mL). The combined organic layers were dried ($Na_2SO_4$), filtered and the solvents evaporated in vacuo to yield rac-2-amino-2-(3-bromo-phenyl)-propionic acid methyl ester (10.6 g, 46% yield) as an oil.

Example A3

Preparation of intermediate 3: rac-2-amino-2-(3-bromophenyl)propan-1-ol

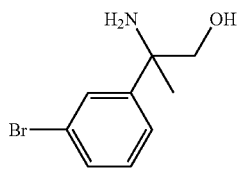

Lithium aluminium hydride (1 M in THF; 22 mL, 22 mmol) was added dropwise to a stirred solution of rac-2-amino-2-(3-bromo-phenyl)-propionic acid methyl ester (7.5 g, 29.1 mmol) in THF (200 mL) at −15° C. The mixture was left warming up slowly to 0° C. during 1 hour. Then more THF (150 mL) was added and sat. $Na_2SO_4$ was added dropwise until no more hydrogen was formed. Then anhydrous $Na_2SO_4$ was added and left stirring overnight at room temperature. The mixture was filtered over diatomaceous earth, rinsed with THF and the solvent evaporated in vacuo. The crude product was purified by flash column chromatography (silica gel; 7 M solution of ammonia in methanol in DCM 0/100 to 3/97). The desired fractions were collected and concentrated in vacuo to yield rac-2-amino-2-(3-bromo-phenyl)-propan-1-ol (5.70 g, 85% yield) as an oil.

Example A4

Preparation of intermediate 4: (R)-2-amino-2-(3-bromophenyl)propan-1-ol

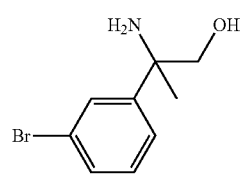

A sample of rac-2-amino-2-(3-bromo-phenyl)-propan-1-ol (15.4 g) was separated into the corresponding enantiomers by preparative SFC on (Chiralpak® Daicel AD×250 mm) Mobile phase ($CO_2$, MeOH with 0.2% $iPrNH_2$) to yield (R)-2-amino-2-(3-bromo-phenyl)-propan-1-ol (7.21 g, 40% yield).

$\alpha_D$: −14.9° (589 nm, c 0.2946 w/v %, MeOH, 20° C.).

Example A5

Preparation of intermediate 5: rac-tert-butyl N-[1-(3-bromophenyl)-2-hydroxy-1-methylethyl]carbamate

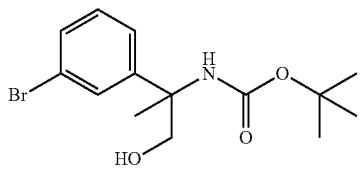 [SMILES: CC(C)(C)OC(=O)NC(C)(CO)c1cccc(Br)c1]

Di-tert-butyldicarbonate (4.84 g, 22.16 mmol) was added portionwise to a stirred solution of rac-2-amino-2-(3-bromophenyl)-propan-1-ol (1.7 g, 7.39 mmol) in a mixture of sat $NaHCO_3$ (15 mL) and THF (15 mL) at 0° C. The mixture was stirred at 0° C. for 10 minutes and at room temperature for 15 hours. The mixture was cooled in an ice water bath and acidified with stirring till pH 1-2 with $KHSO_4$. The organic layer was separated and the aqueous layer was further extracted with AcOEt. The combined organic layers were separated, dried ($MgSO_4$), filtered and the solvents evaporated in vacuo. The crude product was purified by flash column chromatography (silica; AcOEt in DCM 0/100 to 20/80). The desired fractions were collected and concentrated in vacuo to yield rac-[1-(3-bromo-phenyl)-2-hydroxy-1-methyl-ethyl]-carbamic acid tert-butyl ester (2.36 g, 93% yield) as a colourless oil.

Example A6

Preparation of intermediate 6: rac-tert-butyl N-[1-(3-bromophenyl)-1-methyl-2-oxo-ethyl]carbamate

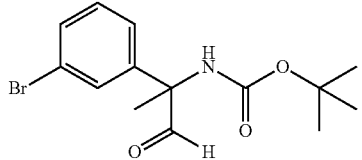 [SMILES: CC(C)(C)OC(=O)NC(C)(C=O)c1cccc(Br)c1]

Dess-Martin periodinane (3.55 g, 8.36 mmol) was added portionwise over 5 minutes to a solution of rac-[1-(3-bromophenyl)-2-hydroxy-1-methyl-ethyl]-carbamic acid tert-butyl ester (2.3 g, 6.97 mmol) in dry DCM (45 mL) at 0° C. The mixture was stirred at 0° C. for 10 minutes and at room temperature for 1 hour. The reaction mixture was quenched with NaHCO$_3$ (aq. sat. solution) followed by NaHSO$_3$ (aq. sat. solution). Then Et$_2$O was added and the mixture was stirred at room temperature for 30 minutes. The organic layer was separated and the aqueous layer was further extracted with Et$_2$O. The combined organic layers were separated, dried (MgSO$_4$), filtered and the solvents evaporated in vacuo. The crude product was purified by flash column chromatography (silica gel; DCM). The desired fractions were collected and concentrated in vacuo to yield rac-[1-(3-bromo-phenyl)-1-methyl-2-oxo-ethyl]-carbamic acid tert-butyl ester (2 g, 88% yield) as a colourless oil.

Example A7

Preparation of intermediate 7: rac-tert-butyl N-[1-(3-bromophenyl)-2-hydroxy-1-methyl-but-3-ynyl]carbamate

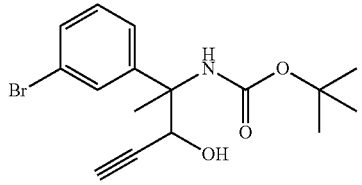 [SMILES: C#CC(O)C(C)(NC(=O)OC(C)(C)C)c1cccc(Br)c1]

Ethynylmagnesium bromide 0.5 M in THF (23.89 mL, 11.94 mmol) was added dropwise to a solution of rac-[1-(3-bromo-phenyl)-1-methyl-2-oxo-ethyl]-carbamic acid tert-butyl ester (1.96 g, 5.97 mmol) in THF (60 mL) at 0° C. under nitrogen. The mixture was stirred at 0° C. for 15 minutes and at room temperature for 30 minutes. The mixture was diluted with NH$_4$Cl (aq. sat. solution) and extracted with DCM. The organic layer was separated, dried (MgSO$_4$), filtered and the solvents evaporated in vacuo to yield rac-[1-(3-bromo-phenyl)-2-hydroxy-1-methyl-but-3-ynyl]-carbamic acid tert-butyl ester (2.11 g, 99% yield) as an oil, which was used in the next step without further purification.

Example A8

Preparation of intermediate 8: rac-tert-butyl N-[1-(3-bromophenyl)-1-methyl-2-oxobut-3-ynyl]carbamate

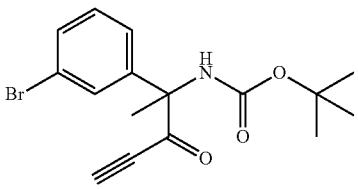 [SMILES: C#CC(=O)C(C)(NC(=O)OC(C)(C)C)c1cccc(Br)c1]

Dess-Martin periodinane (3.04 g, 7.16 mmol) was added portionwise over 5 minutes to a solution of rac-[1-(3-bromophenyl)-2-hydroxy-1-methyl-but-3-ynyl]-carbamic acid tert-butyl ester (2.12 g, 5.97 mmol) in dry DCM (20 mL) at 0° C. The mixture was stirred at 0° C. for 10 minutes and at room temperature for 1 hour. The reaction mixture was quenched with NaHCO$_3$ (aq. sat. solution) followed by NaHSO$_3$ (aqueous sat. soltn.). Then Et$_2$O was added and the mixture was stirred at room temperature for 30 minutes. The organic layer was separated and the aqueous layer was further extracted with Et$_2$O. The combined organic layers were separated, dried (MgSO$_4$), filtered and the solvents evaporated in vacuo. The crude product was purified by flash column chromatography (silica gel; DCM). The desired fractions were collected and concentrated in vacuo to yield rac-[1-(3-bromo-phenyl)-1-methyl-2-oxo-but-3-ynyl]-carbamic acid tert-butyl ester (1.89 g, 90% yield) as an oil.

Example A9

Preparation of intermediate 9: rac-tert-butyl N-[1-(3-bromophenyl)-1-(1H-pyrazol-3-yl)ethyl]carbamate

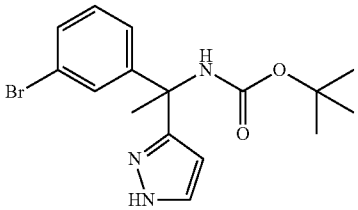 [SMILES: CC(C)(C)OC(=O)NC(C)(c1cccc(Br)c1)c1cc[nH]n1]

Hydrazine hydrate (2.48 mL, 51.10 mmol) was added to a solution of rac-[1-(3-bromo-phenyl)-1-methyl-2-oxo-but-3-ynyl]-carbamic acid tert-butyl ester (1.8 g, 5.11 mmol) in EtOH (30 mL) and the mixture was stirred at room temperature for 1 hour. The solvent was removed in vacuo and the residue was dissolved in DCM and washed with water. The organic layer was separated, dried (MgSO$_4$), filtered and the solvents evaporated in vacuo. The crude product was purified by flash column chromatography (silica gel; AcOEt in DCM 0/100 to 50/50). The desired fractions were collected and concentrated in vacuo to yield rac-[1-(3-bromo-phenyl)-1-

(1H-pyrazol-3-yl)-ethyl]-carbamic acid tert-butyl ester (1.62 g, 87% yield) as a white solid.

Example A10

Preparation of intermediate 10: rac-1-(3-bromophenyl)-1-(1H-pyrazol-3-yl)ethanamine

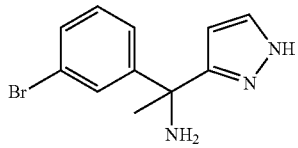

Hydrochloric acid 4 M in dioxane (7.88 mL, 31.54 mmol) was added to rac-[1-(3-bromo-phenyl)-1-(1H-pyrazol-3-yl)-ethyl]-carbamic acid tert-butyl ester (1.65 g, 4.51 mmol) at room temperature. The mixture was stirred at room temperature for 1 hour. The solvent was evaporated in vacuo. The residue was suspended in DCM and washed with NaHCO$_3$ (aq. sat. solution). The organic layer was separated, dried (MgSO$_4$), filtered and the solvents evaporated in vacuo to yield rac-1-(3-bromo-phenyl)-1-(1H-pyrazol-3-yl)-ethylamine (1.2 g, 100% yield) as a white solid, which was used in the next step without further purification.

Example A11

Preparation of intermediate 11: rac-N-[1-(3-bromophenyl)-1-(1H-pyrazol-3-yl)ethyl]-2-chloro-acetamide

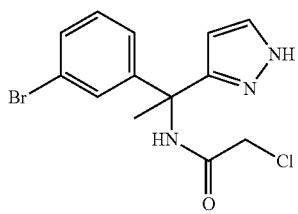 [SMILES: CC(NC(=O)CCl)(c1cccc(Br)c1)c1cc[nH]n1]

DIPEA (1.18 mL, 6.77 mmol) was added to a solution of rac-1-(3-bromo-phenyl)-1-(1H-pyrazol-3-yl)-ethylamine (1.2 g, 4.51 mmol) in DCM (20 mL) and the mixture was cooled in an ice bath. Then chloroacetyl chloride (0.40 mL, 4.96 mmol) was added and the mixture was stirred at 0° C. for 3 hours. The mixture was diluted with NH$_4$Cl (aq. sat. solution) and extracted with DCM. The organic layer was separated, dried (MgSO$_4$), filtered and the solvents evaporated in vacuo. The crude product was purified by flash column chromatography (silica gel; AcOEt in DCM 0/100 to 20/80). The desired fractions were collected and concentrated in vacuo. The residue was dissolved in EtOH (10 mL) and NaHCO$_3$ (aq. sat. solution) (1 mL) and the mixture was stirred at room temperature for 30 minutes. The mixture was diluted with water and the product extracted with DCM. The combined organic layers were concentrated in vacuo to yield rac-N-[1-(3-bromo-phenyl)-1-(1H-pyrazol-3-yl)-ethyl]-2-chloro-acetamide (1.22 g, 79% yield) as a colourless oil, which was used in the next step without further purification.

Example A12

Preparation of intermediate 12: rac-4-(3-bromophenyl)-4-methyl-4,5-dihydro-pyrazolo[1,5-a]pyrazin-6-one

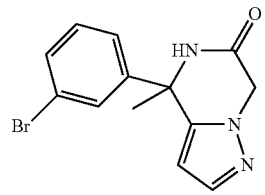

A solution of rac-N-[1-(3-bromo-phenyl)-1-(1H-pyrazol-3-yl)-ethyl]-2-chloro-acetamide (1.22 g, 3.56 mmol) in THF (40 mL) was added dropwise to a suspension of sodium hydride (0.28 g, 7.12 mmol) in THF (40 mL) at 0° C. under nitrogen. The mixture was stirred at 0° C. for 1 hour. The mixture was diluted with water and the product extracted with DCM. The organic layer was separated, dried (MgSO$_4$), filtered and the solvents evaporated in vacuo. The crude product was purified by flash column chromatography (silica gel; AcOEt in DCM 50/50 to 100/0). The desired fractions were collected and concentrated in vacuo to yield rac-4-(3-bromo-phenyl)-4-methyl-4,5-dihydro-pyrazolo[1,5-a]pyrazin-6-one (0.7 g, 64% yield) as a white solid.

Example A13

Preparation of intermediate 13: rac-4-(3-bromophenyl)-4-methy-1-4,5-dihydro-pyrazolo[1,5-a]pyrazine-6-thione

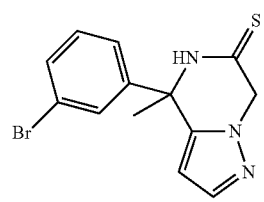 [SMILES: CC1(c2cccc(Br)c2)NC(=S)Cn2nccc21]

Phosphoruspentasulfide (1.02 g, 4.57 mmol) was added to a solution of rac-4-(3-bromophenyl)-4-methyl-4,5-dihydro-pyrazolo[1,5-a]pyrazin-6-one (0.7 g, 2.29 mmol) in pyridine (10 mL) and the mixture was heated at 95° C. for 18 hours. Then the solvent was evaporated in vacuo and the residue was purified by flash column chromatography (silica gel; AcOEt in DCM 0/100 to 100/0). The desired fractions were collected and concentrated in vacuo to yield rac-4-(3-bromo-phenyl)-

4-methyl-4,5-dihydro-pyrazolo[1,5-a]pyrazine-6-thione (0.45 g, 61% yield) as a white solid.

Example A14

Preparation of intermediate 14: rac-4-(3-bromophenyl)-4-methyl-4,7-dihydro-pyrazolo[1,5-a]pyrazin-6-amine

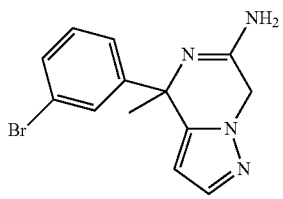 [SMILES: CC1(c2cccc(Br)c2)N=C(N)Cn2nccc21]

NH₄Cl (0.15 g, 2.79 mmol) was added to a stirred solution of rac-4-(3-bromo-phenyl)-4-methyl-4,5-dihydro-pyrazolo[1,5-a]pyrazine-6-thione (0.45 g, 1.40 mmol) in EtOH (50 mL) and the mixture was heated at 80° C. for 28 hours. The solvent was removed in vacuo and the residue was dissolved in DCM and washed with water. The organic layer was separated, dried (MgSO₄), filtered and the solvents evaporated in vacuo. The crude product was purified by flash column chromatography (silica gel; 7 M solution of ammonia in methanol in AcOEt 0/100 to 20/80). The desired fractions were collected and concentrated in vacuo to yield rac-4-(3-bromophenyl)-4-methyl-4,7-dihydro-pyrazolo[1,5-a]pyrazin-6-ylamine (0.42 g, 99% yield) as a yellow solid.

Example A15

Preparation of intermediate 15: rac-4-[3-(benzhydrylideneamino)-phenyl]-4-methyl-4,7-dihydropyrazolo[1,5-a]pyrazin-6-amine

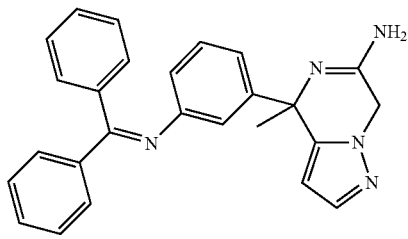 [SMILES: CC1(c2cccc(N=C(c3ccccc3)c3ccccc3)c2)N=C(N)Cn2nccc21]

Toluene (10 mL) was added to a mixture of rac-4-(3-bromo-phenyl)-4-methyl-4,7-dihydro-pyrazolo[1,5-a]pyrazin-6-ylamine (0.39 g, 1.28 mmol), tris(dibenzylideneacetone)dipalladium(0) (0.12 g, 0.13 mmol), rac-2,2'-bis(diphenylphosphino)-1,1'-binaphthyl (0.24 g, 0.38 mmol) and sodium tert-butoxide (0.22 g, 2.3 mmol) in a sealed tube and under nitrogen at room temperature. The mixture was flushed with nitrogen for a few minutes and then benzophenone imine (0.43 mL, 2.56 mmol) was added and the mixture was stirred at 100° C. for 2 hours. After cooling the mixture was diluted with water and extracted with DCM. The organic layer was separated, dried (MgSO₄), filtered and the solvents evaporated in vacuo. The crude product was purified by flash column chromatography (silica; 7 M solution of ammonia in methanol in DCM 0/100 to 3/97). The desired fractions were collected and concentrated in vacuo to yield rac-4-[3-(benzhydrylidene-amino)-phenyl]-4-methyl-4,7-dihydro-pyrazolo[1,5-a]pyrazin-6-ylamine (0.37 g, 70% yield) as a yellow foam.

Example A16

Preparation of intermediate 16: rac-4-(3-aminophenyl)-4-methyl-4,7-dihydro-pyrazolo[1,5-a]pyrazin-6-amine

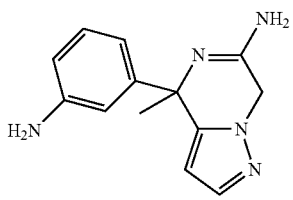 [SMILES: CC1(c2cccc(N)c2)N=C(N)Cn2nccc21]

Hydrochloric acid 37% in H₂O (0.14 mL) was added to a solution of rac-4-[3-(benzhydrylidene-amino)-phenyl]-4-methyl-4,7-dihydro-pyrazolo[1,5-a]pyrazin-6-ylamine (0.37 g, 0.9 mmol) in isopropanol (10 mL). The mixture was stirred at room temperature for 3 hours. Et₂O was added and the mixture was stirred for 15 minutes. The solid precipitated was filtered, washed with Et₂O and dried in vacuo. The residue was suspended in DCM and washed with NaHCO₃ (aq. sat. solution). The organic layer was separated, dried (MgSO₄), filtered and the solvents evaporated in vacuo to yield (0.21 g, 97% yield) as a white solid which was used in the next step without further purification.

Example A17

Preparation of intermediate 17: 1H-pyrazole-3-carboxylic acid

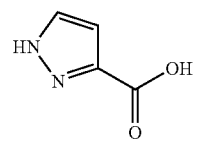

A solution of potassium permanganate (16.17 g, 102.31 mmol) in water (150 mL) was added to a solution of 3-methylpyrazole (4.2 g, 51.15 mmol) in water (100 mL) and the mixture was refluxed overnight. After cooling to room temperature the insoluble material was removed by filtration. The filtrate was concentrated to 30 mL and 2 N HCl was added until a solid was precipitated. The solid was filtered, washed with cold water and dried in vacuo to yield 1H-pyrazole-3- carboxylic acid (3.1 g, 54% yield) as a white solid which was used in the next step without further purification.

Example A18

Preparation of intermediate 18: methyl 1H-pyrazole-3-carboxylate

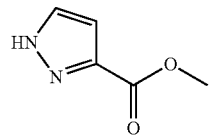

Sulfuric acid (5.8 mL) was added dropwise to a stirred solution of 1H-pyrazole-3-carboxylic acid (1 g, 8.92 mmol) in MeOH (65 mL) at 0° C. After the addition was completed the mixture was allowed to warm to room temperature and stirred for 18 hours. The mixture was concentrated in vacuo and the residue was dissolved in water and basified with NaHCO$_3$ (aq. sat. solution). The mixture was extracted with AcOEt. The organic layer was separated, dried (MgSO$_4$), filtered and the solvents evaporated in vacuo to yield 1H-pyrazole-3-carboxylic acid methyl ester (0.7 g, 62% yield) as a white solid which was used in the next step without further purification.

Example A19

Preparation of intermediate 19: methyl 1-(dimethylsulfamoyl)-1H-pyrazole-3-carboxylate

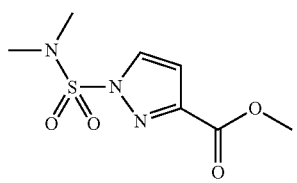

Sodium hydride (1.57 g, 41.03 mmol) was added to a solution of 1H-pyrazole-3-carboxylic acid methyl ester (3.45 g, 27.36 mmol) in THF (20 mL) at 0° C. The mixture was stirred at 0° C. for 30 minutes. Then dimethylsulfamoyl chloride (4.41 mL, 41.03 mmol) was added and the mixture was allowed to warm to room temperature and stirred for 18 hours. The mixture was diluted with water and the product extracted with AcOEt. The organic layer was separated, dried (MgSO$_4$), filtered and the solvents evaporated in vacuo. The crude product was purified by flash column chromatography (silica gel; AcOEt in DCM 0/100 to 10/90). The desired fractions were collected and concentrated in vacuo to yield 1-dimethylsulfamoyl-1H-pyrazole-3-carboxylic acid methyl ester (4.8 g, 75% yield) as a colourless oil.

Example A20

Preparation of intermediate 20: 1-(dimethylsulfamoyl)-N-methoxy-N-methyl-1H-pyrazole-3-carboxylate

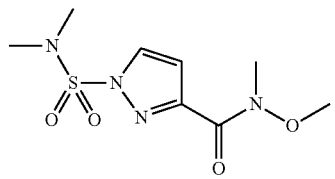

1-Dimethylsulfamoyl-1H-pyrazole-3-carboxylic acid methyl ester (4 g, 17.15 mmol) and N,O-dimethylhydroxylamine hydrochloride (2.18 g, 22.29 mmol) were slurried in DCM (20 mL). The mixture was flushed with nitrogen and cooled to −78° C. Then a solution of isopropylmagnesium chloride (2M in THF) (24.01 mL, 48.02 mmol) was added dropwise. When the addition was completed the mixture was allowed to warm to room temperature and stirred overnight. The mixture was quenched with NH$_4$Cl (aq. sat. solution) and the product was extracted with AcOEt. The organic layer was separated, dried (MgSO$_4$), filtered and the solvents evaporated in vacuo. The crude product was purified by flash column chromatography (silica gel; AcOEt in DCM 0/100 to 100/0). The desired fractions were collected and concentrated in vacuo to yield 1-dimethylsulfamoyl-1H-pyrazole-3-carboxylic acid methoxy-methyl-amide (3.2 g, 71% yield) as a pale yellow oil.

Example A21

Preparation of intermediate 21: 3-(3-chlorophenyl)carbonyl]-N,N-dimethyl-1H-pyrazole-1-sulfonamide

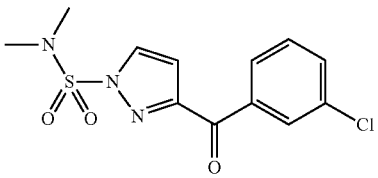 [SMILES: CN(C)S(=O)(=O)n1ccc(C(=O)c2cccc(Cl)c2)n1]

A solution of 3-chlorophenylmagnesium bromide (0.5 M in THF) (15.89 mL, 7.95 mmol) was added to a solution of 1-dimethylsulfamoyl-1H-pyrazole-3-carboxylic acid methoxy-methyl-amide (1.60 g, 6.11 mmol) in THF (20 mL) at −78° C. and under nitrogen. The mixture was stirred at −78° C. for 1 hour and then further stirred at room temperature for 5 hours. The mixture was quenched with NH$_4$Cl (aq. sat. solution) and the product was extracted with AcOEt. The organic layer was separated, dried (MgSO$_4$), filtered and the solvents evaporated in vacuo. The crude product was purified by flash column chromatography (silica gel; AcOEt in DCM 0/100 to 10/90). The desired fractions were collected and

Example A22

Preparation of intermediate 22: 3-{[(tert-butylsulfinyl)imino](3-chlorophenyl)methyl}-N,N-dimethyl-1H-pyrazole-1-sulfonamide

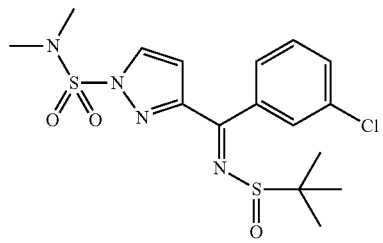 [SMILES: CN(C)S(=O)(=O)n1ccc(/C(=N/S(=O)C(C)(C)C)c2cccc(Cl)c2)n1]

Titanium(IV)isopropoxide (3.22 mL, 10.71 mmol) was added to a mixture of 3-(3-chloro-benzoyl)-1H-pyrazole-1-sulfonic acid dimethylamide (1.68 g, 5.35 mmol) and 2-methyl-2-propanesulfinamide (0.71 g, 5.89 mmol) in toluene (32 mL) under nitrogen. The mixture was stirred at 110° C. for 24 hours. The mixture was cooled and poured into brine while rapidly stirring. The mixture was filtered through diatomaceous earth and the filter cake was washed with AcOEt. The filtrate was transferred to a separation funnel where the organic layer was separated, dried (MgSO$_4$), filtered and the solvents evaporated in vacuo. The crude product was purified by flash column chromatography (silica gel; AcOEt in DCM 0/100 to 10/90). The desired fractions were collected and concentrated in vacuo to yield 3-[(3-chloro-phenyl)-(2-methyl-propane-2-sulfinylimino)-methyl]-pyrazole-1-sulfonic acid dimethylamide (2.17 g, 97% yield) as a yellow oil.

Example A23

Preparation of intermediate 23: 3-[1-(tert-butylsulfinylamino)-1-(3-chlorophenyl)ethyl]-N,N-dimethyl-1H-pyrazole-1-sulfonamide

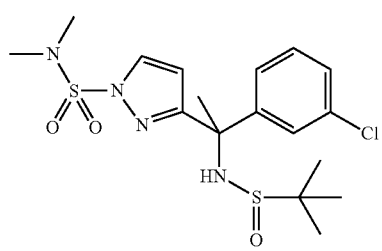 [SMILES: CN(C)S(=O)(=O)n1ccc(C(C)(NS(=O)C(C)(C)C)c2cccc(Cl)c2)n1]

Methylmagnesium bromide (15.08 mL, 21.11 mmol) was added to a solution of 3-[(3-chloro-phenyl)-(2-methyl-propane-2-sulfinylimino)-methyl]-pyrazole-1-sulfonic acid dimethylamide (2.2 g, 5.28 mmol) in THF (25 mL) at 0° C. under nitrogen. The mixture was stirred at 0° C. for 2 hours, quenched with NH$_4$Cl (aq. sat. solution) and the product was extracted with DCM. The organic layer was separated, dried (MgSO$_4$), filtered and the solvents evaporated in vacuo. The crude product was purified by flash column chromatography (silica gel; AcOEt in DCM 0/100 to 100/0). The desired fractions were collected and concentrated in vacuo to yield 3-[1-(3-chloro-phenyl)-1-(2-methyl-propane-2-sulfinylamino)-ethyl]-pyrazole-1-sulfonic acid dimethylamide (2.28 g, 99% yield) as a colourless oil which solidified upon standing.

Example A24

Preparation of intermediate 24: rac-1-(3-chlorophenyl)-1-(1H-pyrazol-3-yl)ethanamine

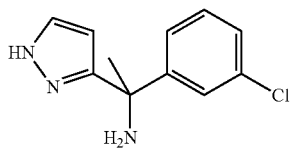

Hydrochloric acid 4 M in dioxane (19.79 mL, 79.15 mmol) was added to a solution of 3-[1-(3-chloro-phenyl)-1-(2-methyl-propane-2-sulfinylamino)-ethyl]-pyrazole-1-sulfonic acid dimethylamide (2.29 g, 5.28 mmol) in MeOH (5 mL) and the mixture was stirred at 80° C. in a sealed tube for 18 hours. The solvent was evaporated in vacuo. The residue was poured into NaHCO$_3$ (aq. sat. solution) and extracted with DCM. The organic layer was separated, dried (MgSO$_4$), filtered and the solvents evaporated in vacuo to yield rac-1-(3-chloro-phenyl)-1-(1H-pyrazol-3-yl)-ethylamine (1 g, 86% yield) as a pale yellow solid which was used in the next step without further purification.

Example A25

Preparation of intermediate 25: rac-2-chloro-N-[1-(3-chlorophenyl)-1-(1H-pyrazol-3-yl)ethyl]-acetamide

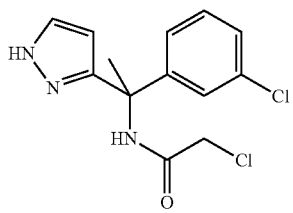 [SMILES: CC(NC(=O)CCl)(c1cccc(Cl)c1)c1cc[nH]n1]

Intermediate 25 was synthesized following the same approach described in the Example A11. Starting from intermediate 24 (1 g, 4.51 mmol) intermediate 25 was obtained (0.73 g, 54% yield) as a white solid.

Example A26

Preparation of intermediate 26: rac-4-(3-chlorophenyl)-4-methyl-4,5-dihydro-pyrazolo[1,5-a]pyrazin-6-one

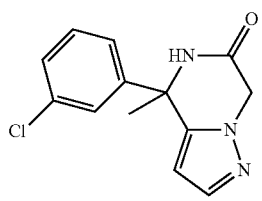 [SMILES: CC1(c2cccc(Cl)c2)NC(=O)Cn2nccc21]

Intermediate 26 was synthesized following the same approach described in the Example A12. Starting from intermediate 25 (0.73 g, 2.43 mmol) intermediate 26 was obtained (0.45 g, 71% yield) as a white solid.

Example A27

Preparation of intermediate 27: rac-4-methyl-4-(3-pyrimidin-5-ylphenyl)-4,5-dihydropyrazolo[1,5-a]pyrazin-6-one

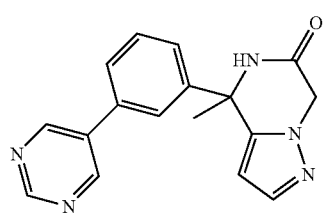 [SMILES: CC1(c2cccc(-c3cncnc3)c2)NC(=O)Cn2nccc21]

Palladium(II) acetate (0.017 g, 0.075 mmol) was added to a stirred suspension of rac-4-(3-chloro-phenyl)-4-methyl-4,5-dihydro-pyrazolo[1,5-a]pyrazin-6-one (0.13 g, 0.50 mmol), pyrimidine-5-boronic acid (0.19 g, 1.49 mmol), 2-dicyclohexylphosphino-2',6'-dimethoxybiphenyl (0.061 g, 0.149 mmol) and potassium phosphate (0.21 g, 0.99 mmol) in toluene (5 mL) and EtOH (0.5 mL) at room temperature and under nitrogen. The mixture was stirred at 150° C. for 30 minutes under microwave irradiation. Then the mixture was filtered through diatomaceous earth and washed with AcOEt. The filtrate was evaporated in vacuo. The residue was purified by flash column chromatography (silica gel; AcOEt). The desired fractions were collected and concentrated in vacuo to yield rac-4-methyl-4-(3-pyrimidin-5-yl-phenyl)-4,5-dihydro-pyrazolo[1,5-a]pyrazin-6-one (0.09 g, 59% yield) as a white solid.

Example A28

Preparation of intermediate 28: rac-4-methyl-4-(3-pyrimidin-5-ylphenyl)-4,5-dihydro-pyrazolo[1,5-a]pyrazine-6-thione

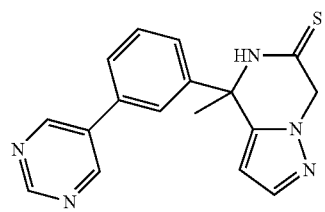 [SMILES: CC1(c2cccc(-c3cncnc3)c2)NC(=S)Cn2nccc21]

Lawesson's reagent (0.14 g, 0.35 mmol) was added to a stirred solution of rac-4-methyl-4-(3-pyrimidin-5-yl-phenyl)-4,5-dihydro-pyrazolo[1,5-a]pyrazin-6-thione (0.09 g, 0.30 mmol) in pyridine (2 mL) at room temperature. The mixture was heated at 95° C. for 18 hours. The solvent was evaporated in vacuo and the crude product was purified by flash column chromatography (silica gel; AcOEt in DCM 0/100 to 20/80). The desired fractions were collected and concentrated in vacuo to yield rac-4-methyl-4-(3-pyrimidin-5-yl-phenyl)-4,5-dihydro-pyrazolo[1,5-a]pyrazin-6-thione (0.02 g, 21% yield) as a white solid.

Example A29

Preparation of intermediate 29: rac-4-[3-(5-methoxy-pyridin-3-yl)phenyl]-4-methyl-4,5-dihydropyrazolo[1,5-a]pyrazin-6-one

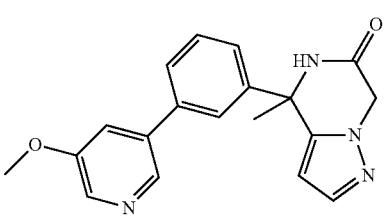 [SMILES: COc1cncc(-c2cccc(C3(C)NC(=O)Cn4nccc43)c2)c1]

Palladium(II) acetate (0.022 g, 0.097 mmol) was added to a stirred suspension of rac-4-(3-chloro-phenyl)-4-methyl-4,5-dihydro-pyrazolo[1,5-a]pyrazin-6-one (0.17 g, 0.65 mmol), 5-methoxypyridine-3-boronic acid (0.15 g, 0.97 mmol), 2-dicyclohexylphosphino-2',6'-dimethoxybiphenyl (0.080 g, 0.195 mmol) and potassium phosphate (0.28 g, 1.30 mmol) in toluene (2 mL) and EtOH (0.2 mL) at room temperature and under nitrogen. The mixture was stirred at 150° C. for 30 minutes under microwave irradiation. Then the mixture was filtered through diatomaceous earth and washed with AcOEt. The filtrate was evaporated in vacuo. The residue was purified by flash column chromatography (silica gel; AcOEt). The desired fractions were collected and concentrated in vacuo to yield rac-4-[3-(5-methoxy-pyridin-3-yl)- phenyl]-4-methyl-4,5-dihydro-pyrazolo[1,5-a]pyrazin-6-one (0.11 g, 51% yield) as a white solid.

Example A30

Preparation of intermediate 30: rac-4-[3-(5-methoxy-pyridin-3-yl)phenyl]-4-methyl-4,5-dihydropyrazolo[1,5-a]pyrazine-6-thione

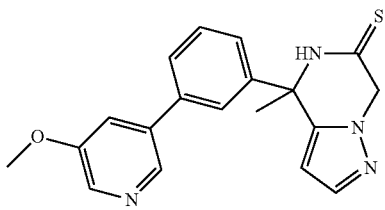 [SMILES: COc1cncc(-c2cccc(C3(C)NC(=S)Cn4nccc43)c2)c1]

Pyridine (3 mL) was added to a mixture of rac-4-[3-(5-methoxy-pyridin-3-yl)-phenyl]-4-methyl-4,5-dihydro-pyrazolo[1,5-a]pyrazin-6-one (0.11 g, 0.31 mmol) and phosphoruspentasulfide (0.07 g, 0.31 mmol) the mixture was heated at 80° C. for 5 hours. Then more phosphoruspentasulfide (0.07 g, 0.31 mmol) was added and the mixture was heated at 100° C. for 18 hours. Then the solvent was evaporated in vacuo and the residue was purified by flash column chromatography (silica gel; MeOH in DCM 0/100 to 3/97). The desired fractions were collected and concentrated in vacuo to yield rac-4-[3-(5-methoxy-pyridin-3-yl)-phenyl]-4-methyl-4,5-dihydro-pyrazolo[1,5-a]-pyrazin-6-thione (0.1 g, 93% yield) as a white solid.

Example A31

Preparation of intermediate 31: rac-4-(5-bromo-2,4-difluorophenyl)-4-methyl-4,5-dihydropyrazolo[1,5-a]pyrazine-6-thione

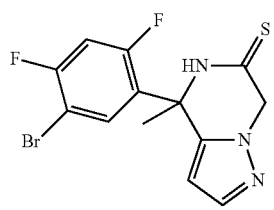 [SMILES: CC1(c2cc(Br)c(F)cc2F)NC(=S)Cn2nccc21]

Phosphoruspentasulfide (2.53 g, 11.40 mmol) was added to a solution of rac-4-(5-bromo-2,4-difluoro-phenyl)-4-methyl-4,5-dihydro-pyrazolo[1,5-a]pyrazin-6-one (3 g, 8.77 mmol), prepared by following the same procedure previously described for the intermediate rac-4-(3-bromo-phenyl)-4-methyl-4,5-dihydro-pyrazolo[1,5-a]pyrazin-6-one, in pyridine (30 mL) and the mixture was heated at 95° C. for 18 hours. Then the solvent was evaporated in vacuo and the residue was purified by flash column chromatography (silica gel; AcOEt in DCM 0/100 to 40/60). The desired fractions were collected and concentrated in vacuo to yield rac-4-(5-bromo-2,4-difluoro-phenyl)-4-methyl-4,5-dihydro-pyrazolo[1,5-a]pyrazin-6-thione (2.4 g, 76% yield) as a white solid.

Example A32

Preparation of intermediate 32: rac-4-(5-bromo-2,4-difluorophenyl)-4-methyl-4,5-dihydropyrazolo[1,5-a]pyrazin-6-amine

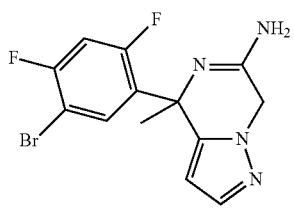 [SMILES: CC1(c2cc(Br)c(F)cc2F)N=C(N)Cn2nccc21]

NH₄Cl (0.72 g, 13.4 mmol) was added to a stirred suspension of rac-4-(5-bromo-2,4-difluoro-phenyl)-4-methyl-4,5-dihydro-pyrazolo[1,5-a]pyrazin-6-thione (2.4 g, 6.7 mmol) in ammonia 2 M in EtOH (67 mL) and the mixture was heated at 85° C. for 18 hours. The solvent was removed in vacuo and the residue was suspended in DCM and washed with water. The organic layer was separated, dried (MgSO₄), filtered and the solvents evaporated in vacuo. The crude product was purified by flash column chromatography (silica gel; 7 M solution of ammonia in methanol in AcOEt 0/100 to 20/80). The desired fractions were collected and concentrated in vacuo to yield rac-4-(5-bromo-2,4-difluoro-phenyl)-4-methyl-4,5-dihydro-pyrazolo[1,5-a]pyrazin-6-yl-amine (1.8 g, 78% yield) as a yellow solid.

Example A33

Preparation of intermediate 33: (R)-tert-butyl N-[1-(3-bromophenyl)-2-hydroxy-1-methylethyl]carbamate

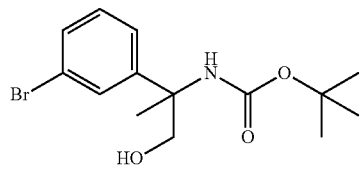 [SMILES: CC(C)(C)OC(=O)NC(C)(CO)c1cccc(Br)c1]

Intermediate 33 was synthesized following the same approach described in the Example A5. Starting from (R)-2-amino-2-(3-bromo-phenyl)-propan-1-ol (4.7 g, 20.43 mmol)

intermediate 33 was obtained (6.4 g, 95% yield) as a colourless oil which solidified upon standing.

Example A34

Preparation of intermediate 34: (R)-tert-butyl N-[1-(3-bromophenyl)-1-methyl-2-oxo-ethyl]carbamate

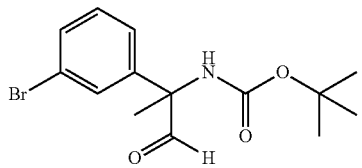 [SMILES: CC(C)(C)OC(=O)NC(C)(C=O)c1cccc(Br)c1]

Intermediate 34 was synthesized following the same approach described in the Example A6. Starting from intermediate 33 (6.4 g, 19.38 mmol) intermediate 34 was obtained (5.7 g, 90% yield) as a colourless oil which solidified upon standing.

Example A35

Preparation of intermediate 35: diastereoisomeric mixture of (1R,2R) and (1R,2S)-tert-butyl N-[1-(3-bromophenyl)-2-hydroxy-1-methyl-but-3-ynyl]carbamate

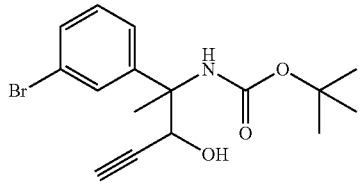

Intermediate 35 was synthesized following the same approach described in the Example A7. Starting from intermediate 34 (5.7 g, 17.38 mmol) intermediate 35 was obtained (5.4 g, 88% yield) as a diastereoisomeric mixture, as an oil which was used in the next step without further purification.

Example A36

Preparation of intermediate 36: (R)-tert-butyl N-[1-(3-bromophenyl)-1-methyl-2-oxo-but-3-ynyl]carbamate

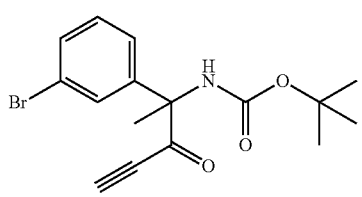

Intermediate 36 was synthesized following the same approach described in the Example A8. Starting from intermediate 35 (5.4 g, 15.24 mmol) intermediate 36 was obtained (5.3 g, 99% yield) as a pale yellow oil.

Example A37

Preparation of intermediate 37: (R)-tert-butyl N-[1-(3-bromophenyl)-1-(1H-pyrazol-3-yl)ethyl]carbamate

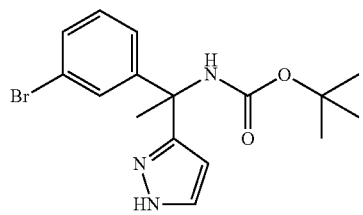 [SMILES: CC(C)(C)OC(=O)NC(C)(c1cccc(Br)c1)c1cc[nH]n1]

Intermediate 37 was synthesized following the same approach described in the Example A9. Starting from intermediate 36 (5.3 g, 15.05 mmol) intermediate 37 was obtained (5 g, 91% yield) as a foam.

Example A38

Preparation of intermediate 38: (R)-1-(3-bromophenyl)-1-(1H-pyrazol-3-yl)ethanamine

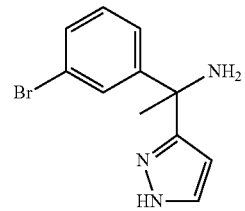

Intermediate 38 was synthesized following the same approach described in the Example A10. Starting from intermediate 37 (5 g, 13.65 mmol) intermediate 38 was obtained (3.5 g, 96% yield) as a white solid which was used in the next step without further purification.

Example A39

Preparation of intermediate 39: (R)—N-[1-(3-bromophenyl)-1-(1H-pyrazol-3-yl)-ethyl]-2-chloroacetamide

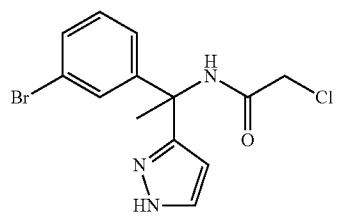 [SMILES: CC(NC(=O)CCl)(c1cccc(Br)c1)c1cc[nH]n1]

Intermediate 39 was synthesized following the same approach described in the Example A11. Starting from inter-

Example A40

Preparation of intermediate 40: (R)-4-(3-bromophenyl)-4-methyl-4,5-dihydro-pyrazolo[1,5-a]pyrazin-6-one

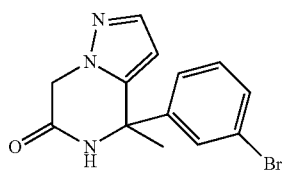 [SMILES: CC1(c2cccc(Br)c2)NC(=O)Cn2nccc21]

Intermediate 40 was synthesized following the same approach described in the Example A12. Starting from intermediate 39 (3.5 g, 10.22 mmol) intermediate 40 was obtained (2.15 g, 69% yield) as a white solid.

Example A41

Preparation of intermediate 41: (R)-4-(3-bromophenyl)-4-methyl-4,5-dihydro-pyrazolo[1,5-a]pyrazine-6-thione

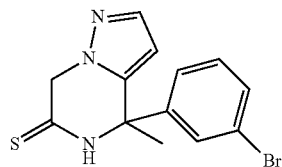 [SMILES: CC1(c2cccc(Br)c2)NC(=S)Cn2nccc21]

Intermediate 41 was synthesized following the same approach described in the Example A13. Starting from intermediate 40 (2.1 g, 6.86 mmol) intermediate 41 was obtained (1.8 g, 81% yield) as a foam.

Example A42

Preparation of intermediate 42: (R)-4-(3-bromophenyl)-4-methyl-4,7-dihydro-pyrazolo[1,5-a]pyrazin-6-amine

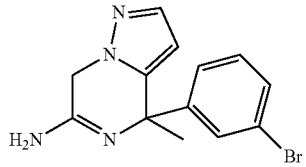 [SMILES: CC1(c2cccc(Br)c2)N=C(N)Cn2nccc21]

32% aqueous ammonia solution (11.9 mL, 201.1 mmol) was added to a stirred mixture of (R)-4-(3-bromo-phenyl)-4-methyl-4,5-dihydro-pyrazolo[1,5-a]pyrazine-6-thione (1.8 g, 5.59 mmol) in 7 N solution of ammonia in methanol (11.97 mL, 83.79 mmol) in a sealed tube. The mixture was stirred at 60° C. for 90 minutes. After cooling to room temperature the mixture was diluted with water and Na$_2$CO$_3$ (aq. sat. solution) and extracted with DCM. The organic layer was separated, dried (Na$_2$SO$_4$), filtered and the solvents evaporated in vacuo. The crude product was purified by flash column chromatography (silica gel; 7 M solution of ammonia in methanol in DCM 0/100 to 2/98 to 3/97 to 10/90). The desired fractions were collected and concentrated in vacuo to yield (R)-4-(3-bromo-phenyl)-4-methyl-4,7-dihydro-pyrazolo[1,5-a]pyrazin-6-ylamine (1.4 g, 82% yield) as a yellow solid.

Example A43

Preparation of intermediate 43: N,N-dimethyl-3-(trifluoromethyl)-1H-pyrazole-1-sulfonamide

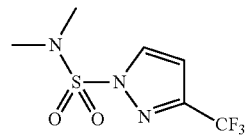

1,4-Diazabicyclo[2.2.2]octane (5.44 g, 48.5 mmol) and dimethylsulfamoyl chloride (4.76 mL, 44.46 mmol) were added to a solution of 3-(trifluoromethyl)pyrazole (5.5 g, 40.42 mmol) in acetonitrile (50 mL) at 0° C. The mixture was allowed to warm to room temperature and stirred for 18 hours. The mixture was concentrated in vacuo and the residue was diluted with water. The product was extracted with AcOEt. The organic layer was separated, dried (MgSO$_4$), filtered and the solvents evaporated in vacuo. The crude product was purified by flash column chromatography (silica gel; DCM). The desired fractions were collected and concentrated in vacuo to yield intermediate 43 (9.4 g, 95% yield) as a colourless oil.

Example A44

Preparation of intermediate 44: 5-[(3-bromophenyl)(hydroxyl)methyl]-N,N-dimethyl-3-(trifluoromethyl)-1H-pyrazole-1-sulfonamide

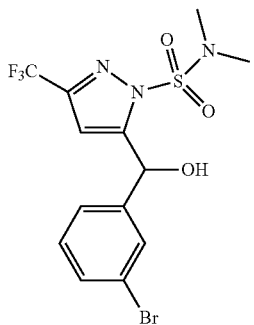 [SMILES: CN(C)S(=O)(=O)n1nc(C(F)(F)F)cc1C(O)c1cccc(Br)c1]

A solution of butyl lithium (2.5 M in hexanes) (15.2 mL, 37.9 mmol) was added to a solution of intermediate 43 (8.4 g, 34.54 mmol) in THF (125 mL) at −78° C. under nitrogen. The mixture was stirred at −78° C. for 45 minutes and then 2-bromobenzaldehyde (6 mL, 51.8 mmol) was added dropwise. The reaction mixture was stirred at −78° C. for 30 minutes and was allowed to warm to room temperature and stirred for 1 hour. The mixture was quenched with NH$_4$Cl (aq. sat. solution) and the product was extracted with AcOEt. The organic layer was separated, dried (MgSO$_4$), filtered and the solvents evaporated in vacuo. The crude product was purified by flash column chromatography (silica gel; DCM in heptanes 0/100 to 10/90). The desired fractions were collected and concentrated in vacuo to yield intermediate 44 (13.2 g, 89% yield) as a colourless oil.

Example A45

Preparation of intermediate 45: 5-[(3-bromophenyl)carbonyl]-N,N-dimethyl-3-(trifluoromethyl)-1H-pyrazole-1-sulfonamide

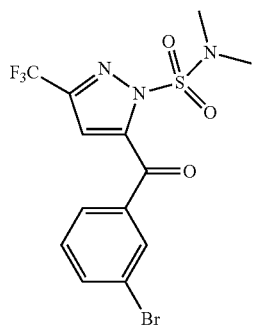 [SMILES: CN(C)S(=O)(=O)n1nc(C(F)(F)F)cc1C(=O)c1cccc(Br)c1]

Manganese dioxide (15.4 g, 169.3 mmol) was added to a solution of intermediate 44 (14.5 g, 33.86 mmol) in 1,4-dioxane (150 mL). The mixture was stirred at 120° C. for 3 hours. The reaction mixture was cooled to 40° C. and filtered through diatomaceous earth. The solvent was evaporated in vacuo to yield intermediate 45 (25.6 g, 97% yield) as a white solid, which was used as such in the next step.

Example A46

Preparation of intermediate 46: 5-[(3-bromophenyl)[(tert-butylsulfinyl)imino]methyl]-N,N-dimethyl-3-(trifluoromethyl)-1H-pyrazole-1-sulfonamide

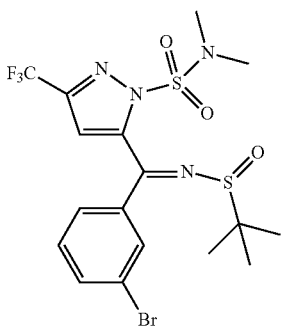 [SMILES: CN(C)S(=O)(=O)n1nc(C(F)(F)F)cc1/C(=N/S(=O)C(C)(C)C)c1cccc(Br)c1]

Titanium(IV)isopropoxide (11.35 mL, 46.9 mmol) was added to a mixture of intermediate 45 (10 g, 23.46 mmol) and 2-methyl-2-propanesulfinamide (3.128 g, 25.81 mmol) in toluene (140 mL) under nitrogen. The mixture was stirred at 110° C. for 8 hours. The mixture was cooled and poured into brine while rapidly stirring. The mixture was filtered through diatomaceous earth and the filter cake was washed with AcOEt. The filtrate was transferred to a separation funnel and the organic layer was separated, dried (MgSO$_4$), filtered and the solvents evaporated in vacuo. The crude product was purified by flash column chromatography (silica gel; AcOEt in DCM 0/100 to 10/90). The desired fractions were collected and concentrated in vacuo to yield intermediate 46 (4 g, 32% yield) as a yellow oil.

Example A47

Preparation of intermediate 47: rac-5-[1-(3-bromophenyl)-1-[(tert-butylsulfinyl)amino]ethyl]-N,N-dimethyl-3-(trifluoromethyl)-1H-pyrazole-1-sulfonamide

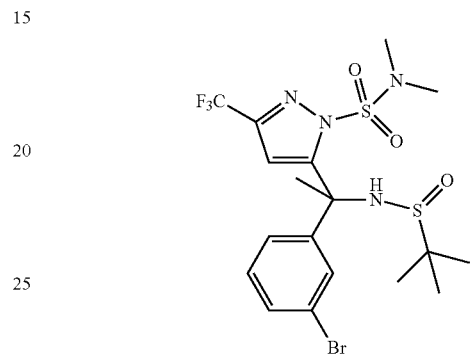

Methylmagnesium bromide (3 M in diethyl ether, 6.3 mL, 18.89 mmol) was added to a solution of intermediate 46 (4 g, 7.56 mmol) in THF (56 mL) at −78° C. under nitrogen. The mixture was stirred at −78° C. for 30 minutes and then was allowed to warm to room temperature and stirred for 18 hours. The reaction mixture was quenched with NH$_4$Cl (aq. sat. solution) and the product was extracted with DCM. The organic layer was separated, dried (MgSO$_4$), filtered and the solvents evaporated in vacuo. The crude product was purified by flash column chromatography (silica gel; AcOEt in DCM 0/100 to 100/0). The desired fractions were collected and concentrated in vacuo to intermediate 47 (3.6 g, 87% yield) as a colourless oil which solidified upon standing.

Example A48

Preparation of intermediate 48: rac-5-[1-amino-1-(3-bromophenyl)ethyl]-N,N-dimethyl-3-(trifluoromethyl)-1H-pyrazole-1-sulfonamide

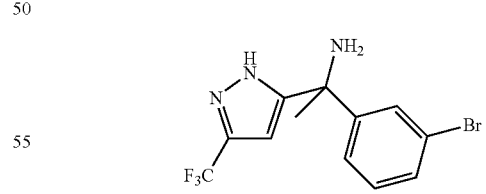

Hydrochloric acid 4 M in dioxane (24.7 mL, 99 mmol) was added to a solution of intermediate 47 (3.6 g, 6.6 mmol) in MeOH (5 mL) and the mixture was stirred at 80° C. in a sealed tube for 18 hours. The solvent was evaporated in vacuo. The residue was poured into NaHCO$_3$ (aq. sat. solution) and extracted with DCM. The organic layer was separated, dried (MgSO$_4$), filtered and the solvents evaporated in vacuo. The crude product was purified by flash column chromatography (silica gel; methanol in DCM 0/100 to 2/98). The desired fractions were collected and concentrated in vacuo to yield to intermediate 48 (1.5 g, 54% yield) as a pale yellow solid.

Example A49

Preparation of intermediate 49: rac-N-{1-(3-bromophenyl)-1-[3-(trifluoromethyl)-1H-pyrazol-5-yl]ethyl}-2-chloroacetamide

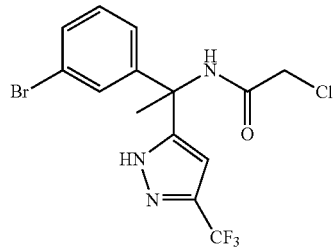 [SMILES: CC(NC(=O)CCl)(c1cccc(Br)c1)c1cc(C(F)(F)F)n[nH]1]

DIPEA (1.9 mL, 11.2 mmol) was added to a solution of intermediate 48 (1.5 g, 4.49 mmol) in DCM (20 mL) and the mixture was cooled in an ice bath. Then chloroacetyl chloride (0.429 mL, 5.38 mmol) was added and the mixture was stirred at 0° C. for 3 hours. The mixture was diluted with NH$_4$Cl (aq. sat. solution) and extracted with DCM. The organic layer was separated, dried (MgSO$_4$), filtered and the solvents evaporated in vacuo. The crude product was purified by flash column chromatography (silica gel; AcOEt in DCM 0/100 to 30/70). The desired fractions were collected and concentrated in vacuo to yield intermediate 49 (1.1 g, 60% yield) as a pale yellow solid.

Example A50

Preparation of intermediate 50: rac-4-(3-bromophenyl)-4-methyl-2-(trifluoromethyl)-4,5-dihydropyrazolo[1,5-a]pyrazin-6-one

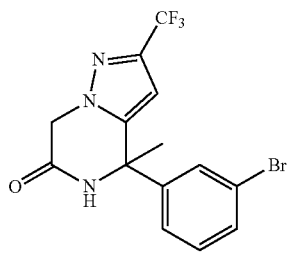 [SMILES: CC1(c2cccc(Br)c2)NC(=O)Cn2nc(C(F)(F)F)cc21]

A solution of intermediate 49 (1.1 g, 2.68 mmol) in THF (40 mL) was added dropwise to a suspension of sodium hydride (0.214 g, 5.36 mmol) in THF (40 mL) at 0° C. under nitrogen. The mixture was stirred at 0° C. for 1 hour. The mixture was diluted with water and the product extracted with DCM. The organic layer was separated, dried (MgSO$_4$), filtered and the solvents evaporated in vacuo. The crude product was purified by flash column chromatography (silica gel; AcOEt in DCM 0/100 to 20/80). The desired fractions were collected and concentrated in vacuo to yield intermediate 50 (0.92 g, 92% yield) as a white solid.

Example A51

Preparation of intermediate 51: rac-4-(3-bromophenyl)-4-methyl-2-(trifluoromethyl)-4,5-dihydropyrazolo[1,5-a]pyrazine-6-thione

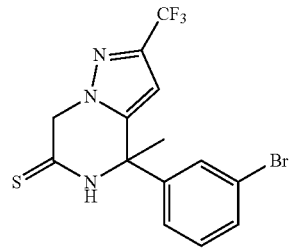 [SMILES: CC1(c2cccc(Br)c2)NC(=S)Cn2nc(C(F)(F)F)cc21]

Phosphoruspentasulfide (0.82 g, 3.69 mmol) was added to a solution of intermediate 50 (0.92 g, 2.46 mmol) in pyridine (10 mL) and the mixture was heated at 90° C. for 18 hours. The reaction mixture was concentrated in vacuo and the residue was purified by flash column chromatography (silica gel; AcOEt in DCM 0/100 to 100/0). The desired fractions were collected and concentrated in vacuo to yield intermediate 51 (0.27 g, 28% yield) as a pale yellow solid.

Example A52

Preparation of intermediate 52: rac-4-(3-bromophenyl)-4-methyl-2-(trifluoromethyl)-4,5-dihydropyrazolo[1,5-a]pyrazin-6-amine

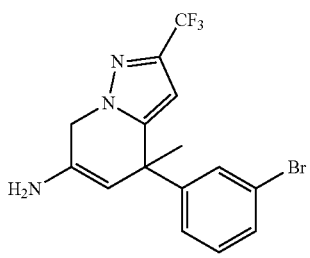 [SMILES: CC1(c2cccc(Br)c2)C=C(N)Cn2nc(C(F)(F)F)cc21]

NH$_4$Cl (0.148 g, 2.77 mmol) was added to a stirred suspension of intermediate 51 (0.27 g, 0.69 mmol) in ammonia 2 M in EtOH (6 mL) and the mixture was heated at 80° C. for 18 hours. The solvent was removed in vacuo and the residue was suspended in DCM and washed with water. The organic layer was separated, dried (MgSO$_4$), filtered and the solvents evaporated in vacuo. The crude product was purified by flash column chromatography (silica gel; 7 M solution of ammonia in methanol in DCM 0/100 to 2/98). The desired fractions were collected and concentrated in vacuo to yield intermediate 52 (0.195 g, 75% yield) as a beige solid.

Example A53

Preparation of intermediate 53: rac-5-[(5-bromo-2-fluorophenyl)(hydroxy)methyl]-N,N-dimethyl-3-(trifluoromethyl)-1H-pyrazole-1-sulfonamide

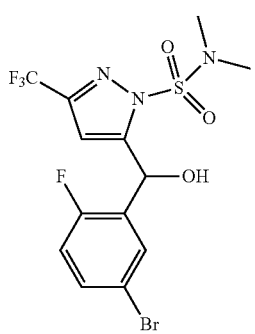 [SMILES: CN(C)S(=O)(=O)n1nc(C(F)(F)F)cc1C(O)c1cc(Br)ccc1F]

Intermediate 53 was synthesized following the same approach described in the Example A44. Starting from intermediate 43 (17 g, 69.9 mmol) intermediate 53 was obtained (28 g, 76% yield) as a colourless oil.

Example A54

Preparation of intermediate 54: rac-5-[(5-Bromo-2-fluorophenyl)carbonyl]-N,N-dimethyl-3-(trifluoromethyl)-1H-pyrazole-1-sulfonamide

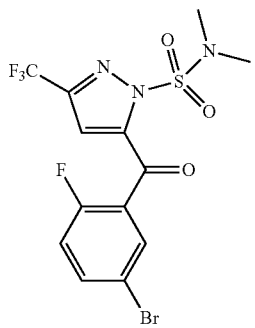 [SMILES: CN(C)S(=O)(=O)n1nc(C(F)(F)F)cc1C(=O)c1cc(Br)ccc1F]

Intermediate 54 was synthesized following the same approach described in the Example A45. Starting from intermediate 53 (28 g, 53.3 mmol) intermediate 54 was obtained (25.6 g, 97% yield) as a white solid, which was used as such in the next step.

Example A55

Preparation of intermediate 55: rac-5-[(5-bromo-2-fluorophenyl)[(tert-butylsulfinyl)imino]methyl]-N,N-dimethyl-3-(trifluoromethyl)-1H-pyrazole-1-sulfonamide

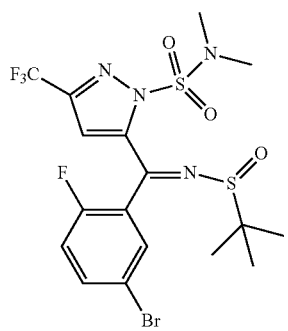 [SMILES: CN(C)S(=O)(=O)n1nc(C(F)(F)F)cc1/C(=N/S(=O)C(C)(C)C)c1cc(Br)ccc1F]

Intermediate 55 was synthesized following the same approach described in the Example A46. Starting from intermediate 54 (25.6 g, 57.6 mmol) intermediate 55 was obtained (21 g, 67% yield) as a pale yellow solid.

Example A56

Preparation of intermediate 56: rac-5-[1-(5-bromo-2-fluorophenyl)-1-[(tert-butylsulfinyl)amino]ethyl]-N,N-dimethyl-3-(trifluoromethyl)-1H-pyrazole-1-sulfonamide

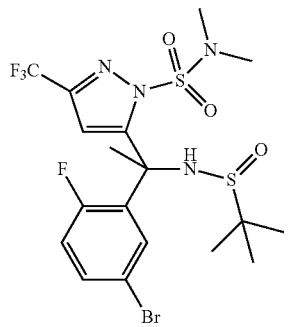 [SMILES: CN(C)S(=O)(=O)n1nc(C(F)(F)F)cc1C(C)(NS(=O)C(C)(C)C)c1cc(Br)ccc1F]

Intermediate 56 was synthesized following the same approach described in the Example A47. Starting from intermediate 55 (21 g, 38.36 mmol) intermediate 56 was obtained (19 g, 88% yield) as a colourless oil which solidified upon standing.

Example A57

Preparation of intermediate 57: rac-1-(5-bromo-2-fluorophenyl)-1-[3-(trifluoromethyl)-1H-pyrazol-5-yl]ethanamine

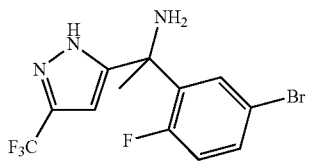

Hydrochloric acid 1.25 M in methanol (159 mL, 199 mmol) was added to intermediate 56 (18.7 g, 33.2 mmol) and the mixture was stirred at 60° C. in a sealed tube for 3 hours. The solvent was evaporated in vacuo. The residue was poured into NaHCO$_3$ (aq. sat. solution) and extracted with DCM. The organic layer was separated, dried (MgSO$_4$), filtered and the solvents evaporated in vacuo to yield intermediate 57 (11.5 g, 98% yield) as a pale yellow solid which was used as such in the next step without further purification.

Example A58

Preparation of intermediate 58: rac-N-{1-(5-bromo-2-fluorophenyl)-1-[3-(trifluoromethyl)-1H-pyrazol-5-yl]ethyl}-2-chloroacetamide

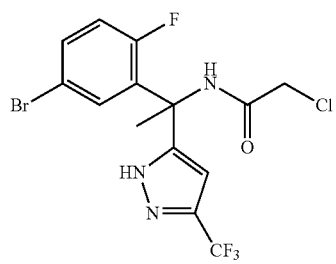 [SMILES: CC(NC(=O)CCl)(c1cc(C(F)(F)F)n[nH]1)c1cc(Br)ccc1F]

Intermediate 58 was synthesized following the same approach described in the Example A49. Starting from intermediate 57 (11.5 g, 32.66 mmol) intermediate 58 was obtained (6.6 g, 47% yield) as a pale yellow solid.

Example A59

Preparation of intermediate 59: rac-4-(5-bromo-2-fluorophenyl)-4-methyl-2-(trifluoromethyl)-4,5-dihydropyrazolo[1,5-a]pyrazin-6-one

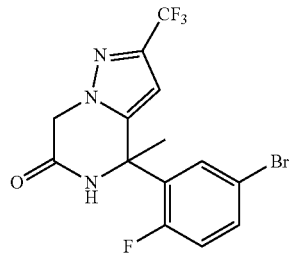 [SMILES: CC1(c2cc(Br)ccc2F)NC(=O)Cn2nc(C(F)(F)F)cc21]

Intermediate 59 was synthesized following the same approach described in the Example A50. Starting from intermediate 58 (6.6 g, 15.4 mmol) intermediate 59 was obtained (6 g, 99% yield) as a white solid.

Example A60

Preparation of intermediate 60: rac-4-(5-bromo-2-fluorophenyl)-4-methyl-2-(trifluoromethyl)-4,5-dihydropyrazolo[1,5-a]pyrazine-6-thione

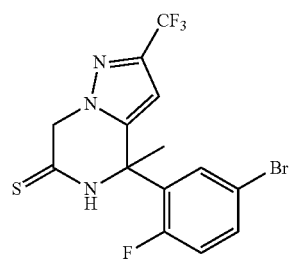 [SMILES: CC1(c2cc(Br)ccc2F)NC(=S)Cn2nc(C(F)(F)F)cc21]

Phosphoruspentasulfide (2.27 g, 10.2 mmol) was added to a solution of intermediate 59 (4 g, 10.2 mmol) in dioxane (80 mL) and the mixture was heated at 80° C. for 18 hours. The reaction mixture was filtered through diatomaceous earth. Then the filtrate was evaporated in vacuo and the residue was purified by flash column chromatography (silica gel; DCM).

The desired fractions were collected and concentrated in vacuo to yield intermediate 60 (2.3 g, 55% yield) as a pale yellow solid.

Example A61

Preparation of intermediate 61: rac-4-(5-bromo-2-fluorophenyl)-4-methyl-2-(trifluoromethyl)-4,5-dihydropyrazolo[1,5-a]pyrazin-6-amine

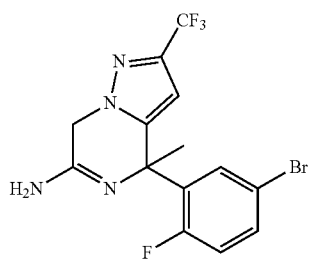 [SMILES: CC1(c2cc(Br)ccc2F)N=C(N)Cn2nc(C(F)(F)F)cc21]

Intermediate 61 was synthesized following the same approach described in the Example A52. Starting from intermediate 60 (2 g, 4.9 mmol) intermediate 61 was obtained (1.5 g, 78% yield) as a white solid.

Example A62

Preparation of intermediate 62: rac-4-[5-(benzhydrylideneamino)-2-fluorophenyl]-4-methyl-2-(trifluoromethyl)-4,7-dihydropyrazolo[1,5-a]pyrazin-6-amine

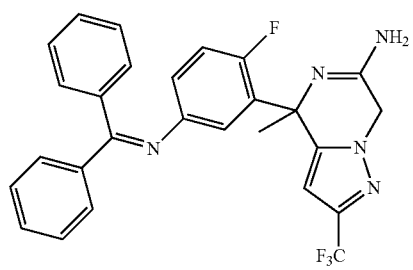 [SMILES: CC1(c2cc(N=C(c3ccccc3)c3ccccc3)ccc2F)N=C(N)Cn2nc(C(F)(F)F)cc21]

Intermediate 62 was synthesized following the same approach described in the Example A15. Starting from intermediate 61 (0.67 g, 1.59 mmol) intermediate 62 was obtained (0.53 g, 67% yield) as a pale yellow solid.

Example A63

Preparation of intermediate 63: rac-4-(5-amino-2-fluorophenyl)-4-methyl-2-(trifluoromethyl)-4,7-dihydropyrazolo[1,5-a]pyrazin-6-amine

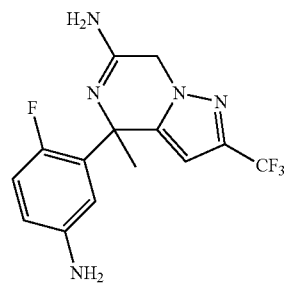 [SMILES: CC1(c2cc(N)ccc2F)N=C(N)Cn2nc(C(F)(F)F)cc21]

Intermediate 63 was synthesized following the same approach described in the Example A16. Starting from intermediate 62 (0.525 g, 1.07 mmol) intermediate 63 was obtained (0.225 g, 64% yield) as a pale yellow solid.

Example A64

Preparation of intermediate 64: (5-bromo-2-fluorophenyl)(oxo)acetic acid

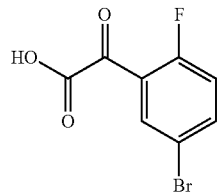 [SMILES: O=C(O)C(=O)c1cc(Br)ccc1F]

5'-Bromo-2'-fluoroacetophenone [(CAS 198477-89-3), 70 g, 322 mmol) and selenium dioxide (71.6 g, 645 mmol) were dissolved in pyridine (520 mL). The reaction mixture was stirred at 100° C. for 2 hours. The solvent was evaporated and aqueous HCl 1N solution was added. The aqueous layer was extracted with EtOAc. The combined organic layers were dried (Mg₂SO₄), filtered and concentrated in vacuo to yield intermediate 64 (62 g, 78% yield), which was used as such in the next reaction.

Example A65

Preparation of intermediate 65: tert-butyl (5-bromo-2-fluorophenyl)(oxo)acetate

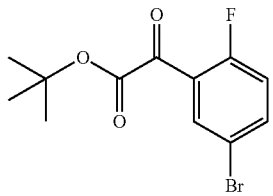 [SMILES: CC(C)(C)OC(=O)C(=O)c1cc(Br)ccc1F]

Thionyl chloride (72 g, 607 mmol) was added dropwise to a stirred solution of intermediate 64 (50 g, 202 mmol) in toluene (500 mL) at 0° C. The mixture was stirred at 60° C. for 1.5 hours. The solvents were evaporated in vacuo. DCM was added and then the mixture was concentrated again in vacuo. The crude was dissolved in DCM (100 mL). Tert-butanol (30 g, 404 mmol), pyridine (16 mL, 202 mmol) and anhydrous DCM (100 mL) were added carefully. The mixture was stirred at rt for 1.5 hours. The solvents were evaporated in vacuo. The crude was purified by flash column chromatography (silica gel; DCM). The desired fractions were collected and concentrated in vacuo to yield intermediate 65 (45.5 g, 74% yield).

Example A66

Preparation of intermediate 66: (S)-1-methylethyl (5-bromo-2-fluorophenyl)[(tert-butylsulfinyl)imino]acetate

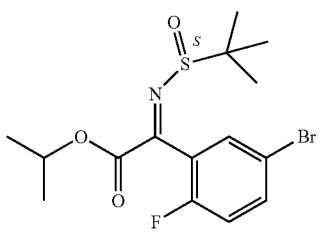

Titanium(IV) isopropoxide (85 mL, 283 mmol) was added to a stirred mixture of intermediate 65 (43 g, 142 mmol) and (S)-2-methyl-2-propanesulfinamide (25.8 g, 212 mmol) in n-heptane (1000 mL). The mixture was stirred at 80° C. for 18 hours. The mixture was partly concentrated in vacuo, then diluted with EtOAc. The mixture was cooled to room temperature, and water was added. The resulting mixture was filtered over a diatomaceous earth pad and rinsed with EtOAc and water. The organic layer was separated, dried (MgSO₄), filtered and concentrated in vacuo. The residue was purified by flash column chromatography (silica gel; eluents n-heptane/EtOAc 90/10 to 80/20). The desired fractions were collected and concentrated in vacuo to yield intermediate 66 (44 g 79% yield).

Example A67

Preparation of intermediate 67: isopropyl (2R)-2-(5-bromo-2-fluorophenyl)-2-[[(S)-tert-butylsulfinyl]amino]-2-cyclopropylacetate

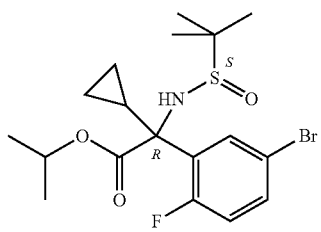

Cyclopropylmagnesium bromide (0.5 M, 174 mL, 87 mmol) was added dropwise to a stirred solution of intermediate 66 in DCM (388 mL) at –78° C. The mixture was stirred at this temperature for 30 minutes, and then the reaction was quenched by the addition of a sat. aq. NH4Cl solution, followed by water. The mixture was extracted with DCM. The organic layer was separated, dried (MgSO₄), filtered and the solvents evaporated in vacuo to yield intermediate 67 (26.4, 98% yield), as a yellowish oil which was used as such in the next step.

Example A68

Preparation of intermediate 68: isopropyl (2R)-2-amino-2-(5-bromo-2-fluorophenyl)-2-cyclopropylacetate

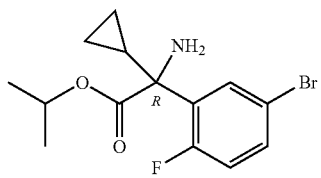

A solution of intermediate 67 (23.9 g, 55 mmol) in a 4M HCl solution in dioxane (27 mL) was stirred at r.t. for 15 min. The solvent was concentrated in vacuo. The crude was dissolved in EtOAc and sat. NaHCO₃ was added. The mixture was stirred for 1 hour. The organic layer was separated, dried (MgSO₄), filtered and concentrated in vacuo to yield intermediate 68 (16.6, 91% yield), as a yellowish oil which was used as such in the next step.

Example A69

Preparation of intermediate 69: (2R)-2-amino-2-(5-bromo-2-fluoro-phenyl)-2-cyclopropyl-ethanol

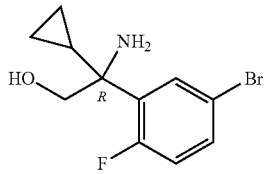

Lithium aluminium hydride (1M in THF, 38 mL, 38 mmol) was added dropwise to a stirred solution of intermediate 68 (16.6 g, 50.2 mmol) in THF (346 mL) at −15° C. The mixture was stirred for 1 hour while slowly warming to 0° C. Solid Na₂SO₄ decahydrate was added to the mixture until no more gas evolution was observed. The mixture was stirred for 30 minutes at room temperature. The mixture was filtered over a diatomaceous earth pad and rinsed with THF. The collected organic layer was evaporated to dryness in vacuo and the resulting crude was purified by flash column chromatography (silica gel; 7N NH₃ in MeOH/DCM 0/100 to 3/97). The desired fractions were collected and concentrated in vacuo to yield intermediate 69 as a yellow oil (13.8 g, quant. yield).

Example A70

Preparation of intermediate 70: tert-butyl[(1R)-1-(5-bromo-2-fluorophenyl)-1-cyclopropyl-2-hydroxy-ethyl]carbamate

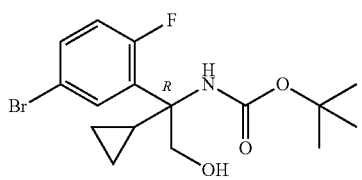

Intermediate 70 was synthesized following the same approach described in the Example A5. Starting from intermediate 69 (4.35 g, 6.03 mmol) intermediate 70 was obtained (3.29 g) as a yellow oil which solidified upon standing.

Example A71

Preparation of intermediate 71: tert-butyl [(1R)-1-(5-bromo-2-fluorophenyl)-1-cyclopropyl-2-oxoethyl]carbamate

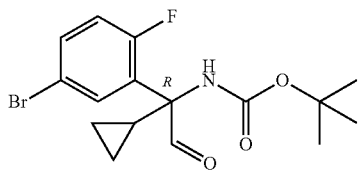

Intermediate 71 was synthesized following the same approach described in the Example A6. Starting from intermediate 70 (4.52 g, 12.08 mmol) intermediate 71 was obtained (4 g, 89% yield) as a pale yellow oil.

Example A72

Preparation of intermediate 72: tert-butyl [(1R)-1-(5-bromo-2-fluorophenyl)-1-cyclopropyl-2-hydroxybut-3-yn-1-yl]carbamate

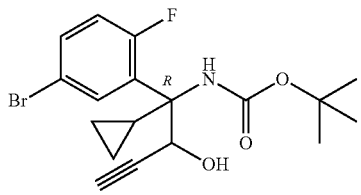

Intermediate 72 was synthesized following the same approach described in the Example A7. Starting from intermediate 71 (4 g, 10.75 mmol) intermediate 72 was obtained (3.9 g, 91% yield) as a diastereoisomeric mixture, as an oil which was used in the next step without further purification.

Example A73

Preparation of intermediate 73: tert-butyl [(1R)-1-(5-bromo-2-fluorophenyl)-1-cyclopropyl-2-oxobut-3-yn-1-yl]carbamate

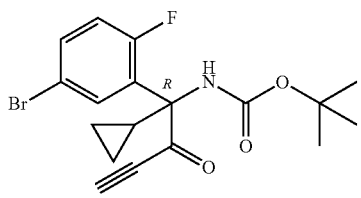

Intermediate 73 was synthesized following the same approach described in the Example A8. Starting from intermediate 72 (3.9 g, 9.8 mmol) intermediate 73 was obtained (3.4 g, 88% yield) as a yellow oil.

Example A74

Preparation of intermediate 74: tert-butyl N—[(R)-(5-bromo-2-fluorophenyl)-cyclopropyl-(1H-pyrazol-3-yl)methyl]carbamate

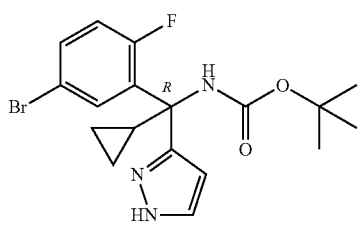

Intermediate 74 was synthesized following the same approach described in the Example A9. Starting from intermediate 73 (3.4 g, 8.58 mmol) intermediate 74 was obtained (3.45 g, 98% yield) as a foam.

Example A75

Preparation of intermediate 75: (R)-(5-bromo-2-fluorophenyl)-cyclopropyl-(1H-pyrazol-3-yl)methanamine

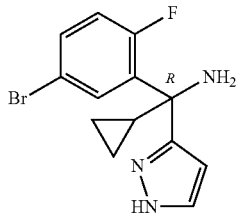

Intermediate 75 was synthesized following the same approach described in the Example A10. Starting from intermediate 74 (3.45 g, 8.41 mmol) intermediate 75 was obtained (2.85 g) as a yellow foam which was used in the next step without further purification.

Example A76

Preparation of intermediate 76: N—[(R)-(5-bromo-2-fluorophenyl)-cyclopropyl-(1H-pyrazol-3-yl)methyl]-2-chloro-acetamide

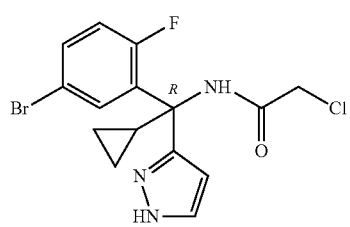

Intermediate 76 was synthesized following the same approach described in the Example A11. Starting from intermediate 75 (2.8 g, 9.03 mmol) intermediate 76 was obtained (1.03 g, 30% yield) as a solid.

Example A77

Preparation of intermediate 77: (R)-4-(5-bromo-2-fluorophenyl)-4-cyclopropyl-4,5-dihydropyrazolo[1,5-a]pyrazin-6-one

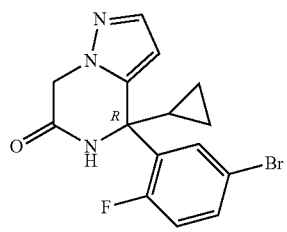

Intermediate 77 was synthesized following the same approach described in the Example A12. Starting from intermediate 76 (0.765 g, 1.98 mmol) intermediate 77 was obtained (0.52 g, 75% yield) as a white solid.

Example A78

Preparation of intermediate 78: (R)-4-(5-bromo-2-fluorophenyl)-4-cyclopropyl-4,5-dihydropyrazolo[1,5-a]pyrazine-6-thione

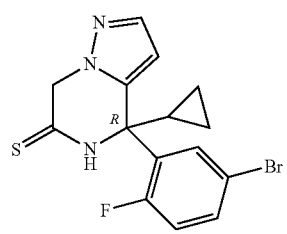

Intermediate 78 was synthesized following the same approach described in the Example A13. Starting from intermediate 77 (0.62 g, 1.77 mmol) intermediate 78 was obtained (0.46 g, 70% yield) as a pale red solid.

Example A79

Preparation of intermediate 79: (R)-4-(5-bromo-2-fluorophenyl)-4-cyclopropyl-4,5-dihydropyrazolo[1,5-a]pyrazin-6-amine

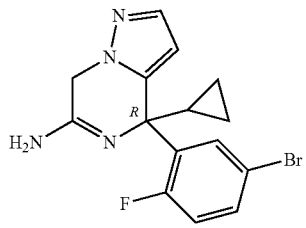

32% aqueous ammonia solution (3 mL, 50.7 mmol) was added to a stirred mixture of intermediate 78 (0.46 g, 1.26 mmol) in 7 N solution of ammonia in methanol (7 mL, 49 mmol) in a sealed tube. The mixture was stirred at 70° C. for 8 hours. After cooling to room temperature the mixture was diluted with water and Na$_2$CO$_3$ (aq. sat. solution) and extracted with DCM. The organic layer was separated, dried (Na$_2$SO$_4$), filtered and the solvents evaporated in vacuo. The crude product was purified by flash column chromatography (silica gel; 7 M solution of ammonia in methanol in DCM 0/100 to 2/98 to 3/97 to 10/90). The desired fractions were collected and concentrated in vacuo to yield intermediate 79 (0.34 g, 78% yield) as a yellow foam.

Example A80

Preparation of intermediate 80: (R)-4-[5-(benzhydrylideneamino)-2-fluorophenyl]-4-cyclopropyl-4,7-dihydropyrazolo[1,5-a]pyrazin-6-amine

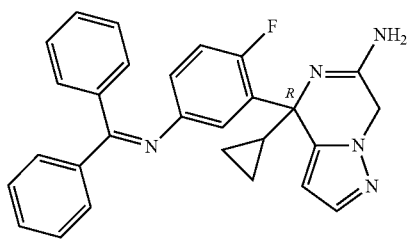

Intermediate 80 was synthesized following the same approach described in the Example A15. Starting from intermediate 79 (0.34 g, 0.974 mmol) intermediate 80 was obtained (0.38 g, 61% yield) as a yellow solid.

Example A81

Preparation of intermediate 81: (R)-4-(5-amino-2-fluorophenyl)-4-cyclopropyl-4,7-dihydropyrazolo[1,5-a]pyrazin-6-amine

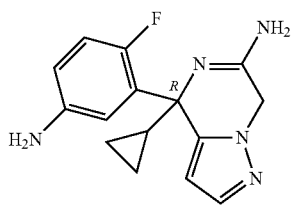

Intermediate 81 was synthesized following the same approach described in the Example A16. Starting from intermediate 80 (0.38 g, 0.845 mmol) intermediate 81 was obtained (0.16 g, 66% yield) as a pale yellow solid.

Preparation of the Final Compounds

Example B1

Preparation of compound 1: rac-4-methyl-4-(3-pyrimidin-5-ylphenyl)-4,7-dihydropyrazolo[1,5-a]pyrazin-6-amine

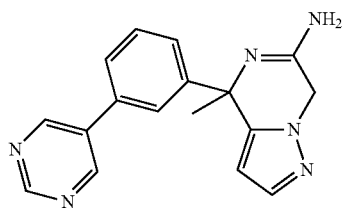 [SMILES: CC1(c2cccc(-c3cncnc3)c2)N=C(N)Cn2nccc21]

NH$_4$Cl (0.007 g, 0.121 mmol) was added to a stirred solution of intermediate 28 (0.026 g, 0.081 mmol) in EtOH (3 mL) and the mixture was heated at 75° C. for 18 hours. The solvent was removed in vacuo and the residue was dissolved in DCM and washed with water. The organic layer was separated, dried (MgSO$_4$), filtered and the solvents evaporated in vacuo. The crude product was purified by flash column chromatography (silica gel; 7 M solution of ammonia in methanol in AcOEt 0/100 to 20/80). The desired fractions were collected and concentrated in vacuo to yield compound 1 (0.02 g, 81% yield) as a pale yellow solid.

Example B2

Preparation of compound 2: rac-4-[3-(5-methoxypyridin-3-yl)-phenyl]-4-methyl-4,7-dihydropyrazolo[1,5-a]pyrazin-6-amine

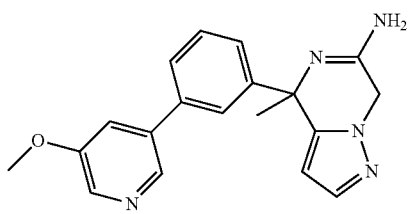 [SMILES: COc1cncc(-c2cccc(C3(C)N=C(N)Cn4nccc43)c2)c1]

Compound 2 was synthesized following the same approach described in the Example B1. Starting from intermediate 30 (0.1 g, 0.285 mmol), compound 2 was obtained (0.06 g, 63% yield) as a white solid.

Example B3

Preparation of compound 3: rac-N-[3-(6-amino-4-methyl-4,7-dihydropyrazolo[1,5-a]pyrazin-4-yl)-phenyl]-5-chloropyridine-2-carboxamide

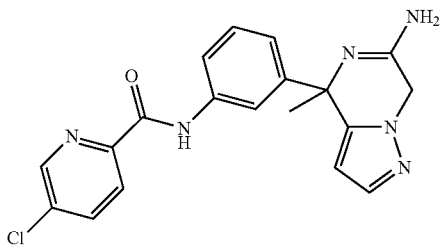 [SMILES: CC1(c2cccc(NC(=O)c3ccc(Cl)cn3)c2)N=C(N)Cn2nccc21]

N,N-dimethylaniline (0.24 mL, 1.92 mmol) was added to a suspension of 5-chloro-2-pyridinecarboxylic acid (0.15 g, 0.96 mmol) and HATU (0.40 g, 1.04 mmol) in DCM (15 mL). The mixture was stirred at room temperature for 10 minutes. Then intermediate 16 (0.21 g, 0.87 mmol) was added and the mixture was stirred at room temperature for 18 hours. The mixture was diluted with NH$_4$Cl (aq. sat. solution) and extracted with DCM. The organic layer was separated, dried (MgSO$_4$), filtered and the solvents evaporated in vacuo. The crude product was purified by flash column chromatography (silica gel; 7 M solution of ammonia in methanol in DCM 0/100 to 5/95). The desired fractions were collected and concentrated in vacuo to yield compound 3 (0.070 g, 21% yield) as a white solid.

Example B4

Preparation of compound 4: rac-4-(2,4-difluoro-5-pyrimidin-5-yl-phenyl)-4-methyl-4,7-dihydropyrazolo[1,5-a]pyrazin-6-amine

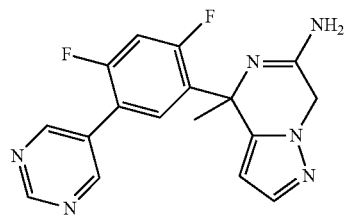 [SMILES: CC1(c2cc(-c3cncnc3)c(F)cc2F)N=C(N)Cn2nccc21]

Tetrakis(triphenylphosphine)palladium(0) (0.025 g, 0.02 mmol) was added to a stirred suspension of intermediate 32 (0.15 g, 0.44 mmol), pyrimidine-5-boronic acid (0.16 g, 1.32 mmol) and potassium carbonate (0.18 g, 1.32 mmol) in 1,4-dioxane (4 mL) and ethanol (0.4 mL) at room temperature under nitrogen. The mixture was stirred at 150° C. for 30 minutes under microwave irradiation. Then the mixture was diluted with water and extracted with DCM. The organic layer was separated, dried (MgSO$_4$), filtered and the solvents evaporated in vacuo. The crude product was purified by flash column chromatography (silica gel; 7 M solution of ammonia in methanol in DCM 0/100 to 3/97). The desired fractions were collected and concentrated in vacuo to yield compound 4 (0.081 g, 54% yield) as a white solid.

Example B5

Preparation of compound 7: (R)-4-(3'-methoxybiphenyl-3-yl)-4-methyl-4,7-dihydropyrazolo[1,5-a]pyrazin-6-amine

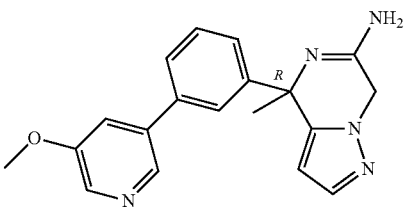

Tetrakis(triphenylphosphine)palladium(0) (0.028 g, 0.025 mmol) was added to a stirred suspension of intermediate 42 (0.15 g, 0.49 mmol), 5-methoxypyridine-3-boronic acid (0.23 g, 1.48 mmol) and potassium carbonate (0.20 g, 1.48 mmol) in 1,4-dioxane (4 mL) and ethanol (0.4 mL) at room temperature under nitrogen. The mixture was stirred at 150° C. for 30 minutes under microwave irradiation. Then the mixture was diluted with water and extracted with DCM. The organic layer was separated, dried (MgSO$_4$), filtered and the solvents evaporated in vacuo. The crude product was purified by flash column chromatography (silica gel; 7 M solution of ammonia in methanol in DCM 0/100 to 3/97). The desired fractions were collected and concentrated in vacuo to yield compound 7 (0.12 g, 73% yield) as a white solid.

Example B6

Preparation of compound 10: (S*)—N-[3-(6-Amino-4-methyl-4,7-dihydropyrazolo[1,5-a]pyrazin-4-yl)-4-fluorophenyl]-5-chloropyridine-2-carboxamide and compound 11: (R*)—N-[3-(6-amino-4-methyl-4,7-dihydropyrazolo[1,5-a]pyrazin-4-yl)-4-fluorophenyl]-5-chloropyridine-2-carboxamide Compound 10

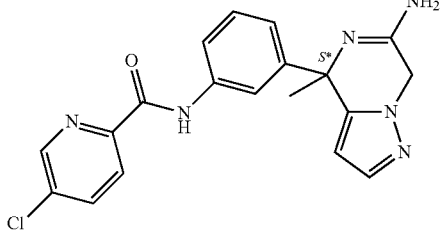

Compound 11

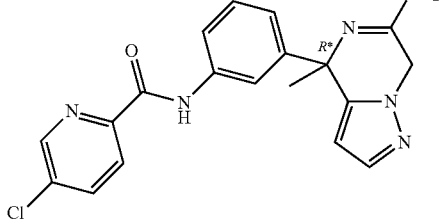

A sample of rac-5-chloro-pyridine-2-carboxylic acid[3-(6-amino-4-methyl-4,7-dihydro-pyrazolo[1,5-a]pyrazin-4-yl)-4-fluoro-phenyl]-amide (0.182 g) was separated into the corresponding enantiomers by preparative SFC on a Chiralpak® AD Daicel column (10 µm, 4.6×250 mm) at 35° C. with a flow rate of 3.0 ml/min. The mobile phase was $CO_2$, 50% Ethanol, 50% EtOH (containing 0.3% $iPrNH_2$) hold 7 min. to yield compound 11 (0.07 g; 38% yield) and compound 10 (0.06 g, 33% yield).

Example B7

Preparation of compound 21: rac-4-[3-(5-methoxy-pyridin-3-yl)-phenyl]-4-methyl-2-(trifluoromethyl)-4,7-dihydropyrazolo[1,5-a]pyrazin-6-amine and compound 22: (R*)-4-[3-(5-methoxypyridin-3-yl)-phenyl]-4-methyl-2-(trifluoromethyl)-4,7-dihydropyrazolo[1,5-a]pyrazin-6-amine and compound 23: (S*)-4-[3-(5-methoxypyridin-3-yl)-phenyl]-4-methyl-2-(trifluoromethyl)-4,7-dihydropyrazolo[1,5-a]pyrazin-6-amine Compound 21

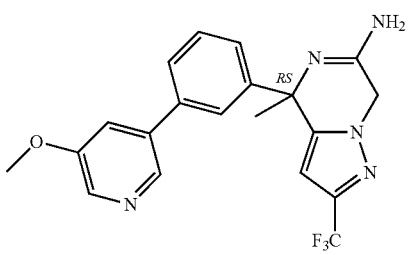

Compound 22

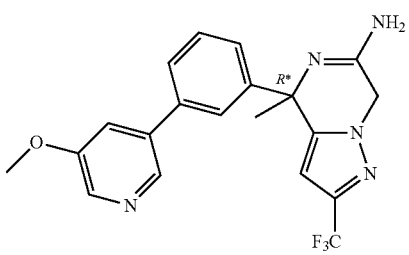

Compound 23

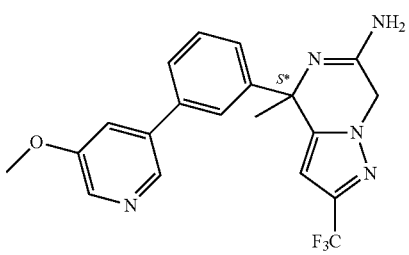

Tetrakis(triphenylphosphine)palladium(0) (0.031 g, 0.027 mmol) was added to a stirred suspension of intermediate 52 (0.2 g, 0.54 mmol), 5-methoxypyridine-3-boronic acid (0.163 g, 1.07 mmol) and potassium carbonate (0.222 g, 1.61 mmol) in 1,4-dioxane (6 mL) and ethanol (0.6 mL) at room temperature under nitrogen. The mixture was stirred at 80° C. for 24 hours. Then the mixture was diluted with water and extracted with DCM. The organic layer was separated, dried ($MgSO_4$), filtered and the solvents evaporated in vacuo. The crude product was purified by flash column chromatography (silica gel; 7 M solution of ammonia in methanol in DCM 0/100 to 3/97). The desired fractions were collected and concentrated in vacuo. The residue was triturated with diethyl ether, sonicated, filtered and dried in vacuo at 50° C. to yield compound 21 (0.13 g, 60% yield) as a white solid. This racemic compound was then purified by preparative SFC on Chiralpak® AD-H column (20×250 mm), mobile phase (CO₂, iPrOH with 0.3% iPrNH₂), yielding compound 22 (0.047 g, 22% yield) and compound 23 (0.051 g, 24% yield) as pure enantiomers (both as solid compounds).

Example B8

Preparation of compound 24: rac-4-[5-(5-chloropyridin-3-yl)-2-fluorophenyl]-4-methyl-2-(trifluoromethyl)-4,7-dihydropyrazolo[1,5-a]pyrazin-6-amine and compound 25: (R*)-4-[5-(5-chloropyridin-3-yl)-2-fluorophenyl]-4-methyl-2-(trifluoromethyl)-4,7-dihydropyrazolo[1,5-a]pyrazin-6-amine and compound 26: (S*)-4-[5-(5-chloropyridin-3-yl)-2-fluorophenyl]-4-methyl-2-(trifluoromethyl)-4,7-dihydropyrazolo[1,5-a]pyrazin-6-amine

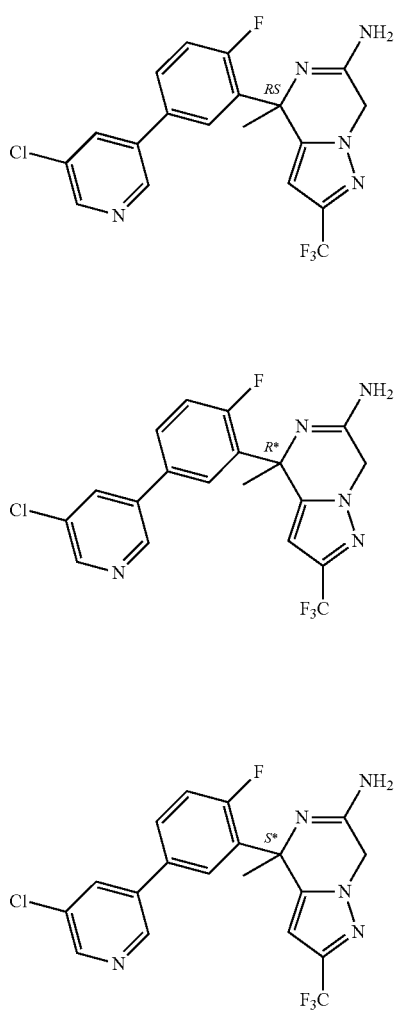

Compound 24

Compound 25

Compound 26

Compound 24 was synthesized following the same approach described in the Example B7. Starting from intermediate 61 (0.3 g, 0.77 mmol), compound 24 was obtained (0.21 g, 64% yield) as a white solid. This racemic compound was then purified by preparative SFC on Chiralpak® AD-H column (20×250 mm), mobile phase (CO₂, iPrOH with 0.3% iPrNH₂), yielding compound 25 (0.089 g, 27% yield) and compound 26 (0.092 g, 28% yield) as pure enantiomers (both as solid compounds).

Example B9

Preparation of compound 27: rac-N-{3-[6-amino-4-methyl-2-(trifluoromethyl)-4,7-dihydropyrazolo[1,5-a]pyrazin-4-yl]-4-fluorophenyl}-3,5-dichloropyridine-2-carboxamide and compound 28: (R*)—N-{3-[6-amino-4-methyl-2-(trifluoromethyl)-4,7-dihydropyrazolo[1,5-a]pyrazin-4-yl]-4-fluorophenyl}-3,5-dichloropyridine-2-carboxamide and compound 29: (S*)—N-{3-[6-amino-4-methyl-2-(trifluoromethyl)-4,7-dihydropyrazolo[1,5-a]pyrazin-4-yl]-4-fluorophenyl}-3,5-dichloropyridine-2-carboxamide

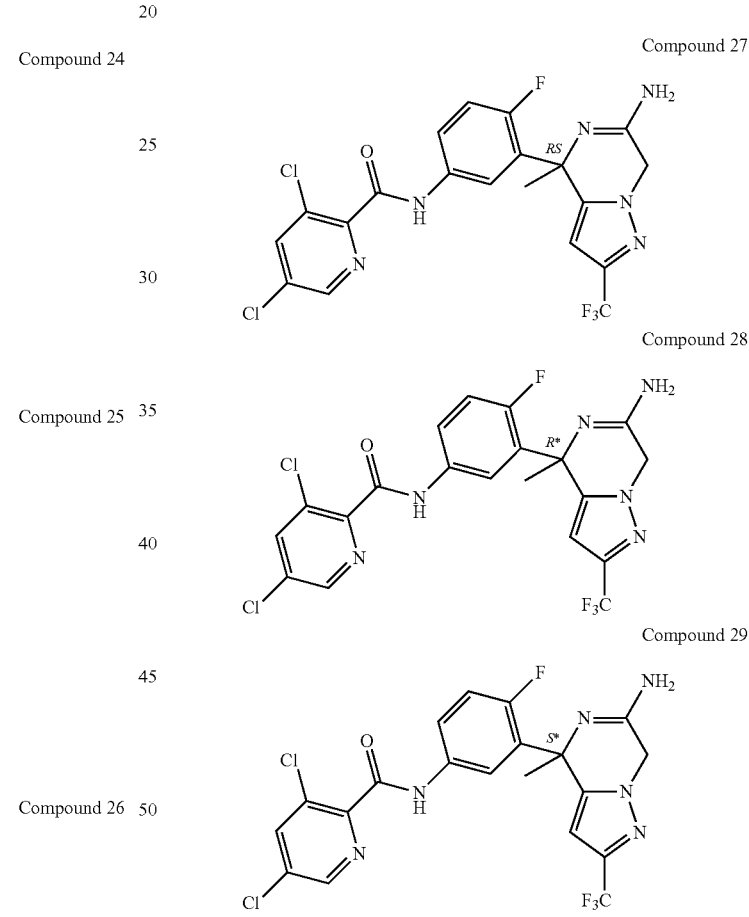

Compound 27

Compound 28

Compound 29

3,5-Dichloro-2-pyridinecarboxylic acid (0.54 g, 0.81 mmol) was dissolved in MeOH (4 mL) and DMTMM (0.223 g, 0.81 mmol) was added. After stirring the mixture for 5 minutes, a solution of intermediate 63 (0.22 g, 0.67 mmol) in MeOH (4 mL) was added at 0° C., and the mixture was stirred for an additional 4 h. The solvent was evaporated in vacuo. The crude product was purified by flash column chromatography (silica gel; 7 M solution of ammonia in methanol/DCM 0/100 to 5/95). The desired fractions were collected and concentrated in vacuo. The residue was crystallized from DIPE to yield compound 27 (0.124 g, 37% yield) as a white solid. This racemic compound was then purified by preparative SFC on Chiralpak® AD-H column (20×250 mm), mobile phase (CO₂, EtOH with 0.3% iPrNH₂), yielding compound 28 (0.038 g, 11% yield) and compound 29 (0.036 g, 11% yield) as pure enantiomers (both as solid compounds).

Example B10

Preparation of compound 33: (R)—N-{3-[6-amino-4-cyclopropyl-4,7-dihydropyrazolo[1,5-a]pyrazin-4-yl]-4-fluorophenyl}-5-chloro-3-fluoropyridine-2-carboxamide

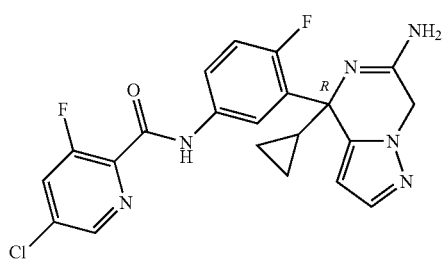

5-Chloro-3-fluoropyridine-2-carboxylic acid (0.052 g, 0.26 mmol) was dissolved in MeOH (1.5 mL) and DMTMM (0.086 g, 0.31 mmol) was added. After stirring the mixture for 5 minutes, a solution of intermediate 81 (0.074 g, 0.26 mmol) in MeOH (1.5 mL) was added at 0° C., and the mixture was stirred for an additional 24 h. The solvent was evaporated in vacuo. The crude product was purified by flash column chromatography (silica gel; 7 M solution of ammonia in methanol/DCM 0/100 to 5/95). The desired fractions were collected and concentrated in vacuo. The residue was dried under vacuum to yield compound 33 (0.084 g, 73% yield) as a white solid.

TABLE 1

| Co. No. | Ex. No. | $X^1$ | $X^3$ | —L—Ar | $C_4$-stereochemistry |
|---|---|---|---|---|---|
| 1 | B1 | CH | CH | pyrimidin-5-yl | RS |
| 2 | B2 | CH | CH | 5-methoxypyridin-3-yl | RS |
| 3 | B3 | CH | CH | 5-chloropyridine-2-carboxamide | RS |
| 4 | B4 | CF | CF | pyrimidin-5-yl | RS |
| 5 | B4 | CF | CF | 5-methoxypyridin-3-yl | RS |
| 6 | B4 | CF | CF | 3-methoxyphenyl | RS |
| 7 | B5 | CH | CH | 3-methoxyphenyl | R |
| 8 | B5 | CH | CH | pyrimidin-5-yl | R |
| 9 | B5 | CH | CH | 5-methoxypyridin-3-yl | R |
| 10 | B6 | CF | CH | 5-chloropyridine-2-carboxamide | S* |
| 11 | B6 | CF | CH | 5-chloropyridine-2-carboxamide | R* |
| 12 | B5 | CF | CF | phenyl | RS |
| 13 | B3 | CF | CH | 5-chloropyridine-2-carboxamide | RS |
| 14 | B4 | CH | CH | 3,5-difluorophenyl | R |

TABLE 1-continued

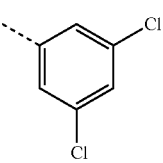

| Co. No. | Ex. No. | X¹ | X³ | —L—Ar | C₄-stereochemistry |
|---|---|---|---|---|---|
| 15 | B4 | CF | CH | 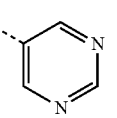 3,5-dichlorophenyl | RS |
| 16 | B4 | CF | CH | 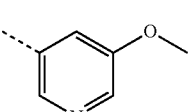 pyrimidin-5-yl | RS |
| 17 | B3 | CH | CH | 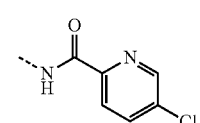 N-H amide, 5-chloropyridin-2-yl | R |
| 18 | B4 | CF | CF | 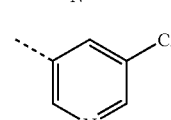 3-cyanophenyl | RS |
| 19 | B5 | CH | CH | 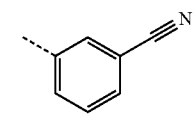 3-OCF₃ phenyl, HCl salt | R |
| 20 | B5 | CH | CH | 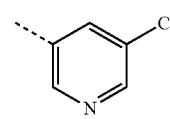 3,5-dichlorophenyl | R |

TABLE 2

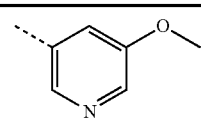

| Co. No. | Ex. No. | X¹ | X³ | —L—Ar | C₄-stereochemistry |
|---|---|---|---|---|---|
| 21 | B7 | CH | CH | 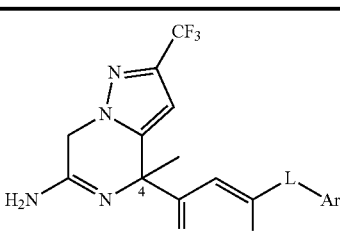 5-methoxypyridin-3-yl | RS |

TABLE 2-continued

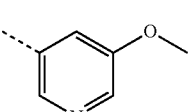

| Co. No. | Ex. No. | X¹ | X³ | —L—Ar | C₄-stereochemistry |
|---|---|---|---|---|---|
| 22 | B7 | CH | CH | 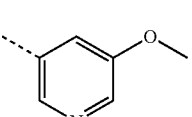 5-methoxypyridin-3-yl | R* |
| 23 | B7 | CH | CH | 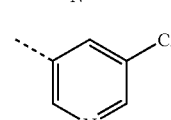 5-methoxypyridin-3-yl | S* |
| 24 | B8 | CF | CH | 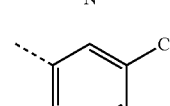 5-chloropyridin-3-yl | RS |
| 25 | B8 | CF | CH | 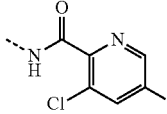 5-chloropyridin-3-yl | R* |
| 26 | B8 | CF | CH | 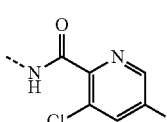 5-chloropyridin-3-yl | S* |
| 27 | B9 | CF | CH | 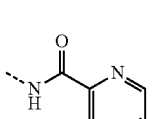 3,5-dichloropyridine-2-carboxamide | RS |
| 28 | B9 | CF | CH | 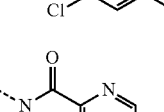 3,5-dichloropyridine-2-carboxamide | R* |
| 29 | B9 | CF | CH | 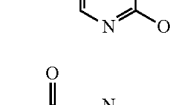 3,5-dichloropyridine-2-carboxamide | S* |
| 30 | B9 | CF | CH | 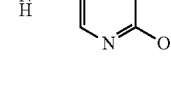 5-methoxypyrazine-2-carboxamide | RS |
| 31 | B9 | CF | CH | 5-methoxypyrazine-2-carboxamide | R* |

TABLE 2-continued

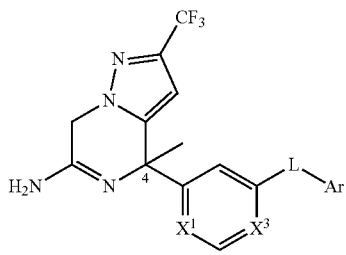

| Co. No. | Ex. No. | X¹ | X³ | —L—Ar | C₄-stereochemistry |
|---|---|---|---|---|---|
| 32 | B9 | CF | CH |  | S* |

TABLE 3

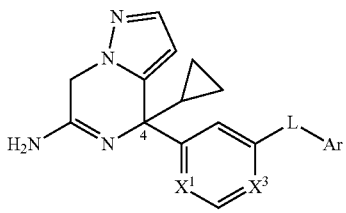

| Co. No. | Ex. No. | X¹ | X³ | —L—Ar | C₄-stereochemistry |
|---|---|---|---|---|---|
| 33 | B10 | CF | CH | 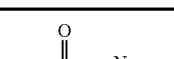 | R |
| 34 | B10 | CF | CH | 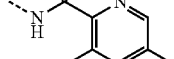 | R |

C. Analytical Part

LCMS

For (LC)MS-characterization of the compounds of the present invention, the following methods were used.

General Procedure A

The HPLC measurement was performed using an HP 1100 (Agilent Technologies) system comprising a pump (quaternary or binary) with degasser, an autosampler, a column oven, a diode-array detector (DAD) and a column as specified in the respective methods. The MS detector was configured with an electrospray ionization source. Nitrogen was used as the nebulizer gas. The source temperature was maintained either at 140° C. or 100° C. Data acquisition was performed with MassLynx-Openlynx software (Waters).

General Procedure B

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software (Waters).

General Procedure C

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with MassLynx-Openlynx software (Waters).

Method 1:

In addition to the general procedure A: Reversed phase HPLC was carried out on a Eclipse Plus-C18 column (3.5 μm, 2.1×30 mm) from Agilent, with a flow rate of 1.0 ml/min, at 60° C. The gradient conditions used are: 95% A (0.5 g/l ammonium acetate solution+5% acetonitrile), 5% B (acetonitrile) to 100% B in 5.0 minutes, kept till 5.15 minutes and equilibrated to initial conditions at 5.3 minutes until 7.0 minutes. Injection volume 2 μl. High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 2:

Same HPLC Gradient as Method 1

High-resolution mass spectra (Time of Flight, TOF detector) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

Method 3:

In addition to the general procedure A: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (0.5 g/l ammonium acetate solution+ 5% acetonitrile), 5% B (mixture of acetonitrile/methanol, 1/1), kept 0.2 minutes, to 100% B in 3.0 minutes, kept till 3.15 minutes and equilibrated to initial conditions at 3.30 minutes until 5.0 minutes. Injection volume 2 μl. Low-resolution mass spectra (single quadrupole, SQD detector) were acquired by scanning from 100 to 1000 in 0.1 second using an interchannel delay of 0.08 second. The capillary needle voltage was 3 kV. The cone voltage was 20 V and 50 V for positive ionization mode and 30 V for negative ionization mode.

Method 4:

In addition to the general procedure B: Reversed phase UPLC was carried out on a RRHD Eclipse Plus-C18 (1.8 μm, 2.1×50 mm) from Agilent, with a flow rate of 1.0 ml/min, at 50° C. without split to the MS detector. The gradient conditions used are: 95% A (0.5 g/l ammonium acetate solution+ 5% acetonitrile), 5% B (acetonitrile), to 40% A, 60% B in 3.8 minutes, to 5% A, 95% B in 4.6 minutes, kept till 5.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 5:

Same gradient as method 4; column used: RRHD Eclipse Plus-C18 (1.8 μm, 2.1×50 mm) from Agilent.

Method 6:

In addition to the general procedure C: Reversed phase UPLC was carried out on a Waters Acquity BEH (bridged ethylsiloxane/silica hybrid) Phenyl-Hexyl column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 ml was used. Cone voltage was 20V for positive and negative ionization mode. Mass spectra were acquired by scanning from 100 to 1000 in 0.2 seconds using an interscan delay of 0.1 seconds.

Method 7:

In addition to the general procedure A: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (0.5 g/l ammonium acetate solution+ 5% acetonitrile), 5% B (mixture of acetonitrile/methanol, 1/1), to 100% B in 5.0 minutes, kept till 5.15 minutes and equilibrated to initial conditions at 5.30 minutes until 7.0 minutes. Injection volume 2 μl. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V for positive ionization mode and 30 V for negative ionization mode.

Melting Points

Values are either peak values or melt ranges, and are obtained with experimental uncertainties that are commonly associated with this analytical method.

Mettler FP 81HT/FP90 Apparatus (Indicated by FP90 in Table 3)

For a number of compounds, melting points were determined in open capillary tubes on a Mettler FP81HT/FP90 apparatus. Melting points were measured with a temperature gradient of 1, 3, 5 or 10° C./minute. Maximum temperature was 300° C. The melting point was read from a digital display.

TABLE 2

Analytical data - $R_t$ means retention time (in minutes), $[M + H]^+$ means the protonated mass of the compound, method refers to the method used for (LC)MS.

| Co. Nr. | $R_t$ | $[M + H]^+$ | Method | Melting Point |
|---|---|---|---|---|
| 1 | 1.77 | 305 | 3 | n.d. |
| 2 | 2.49 | 334 | 2 | 191.8° C. (FP90) |
| 3 | 1.79 | 381 | 4 | 194.9° C. (FP90) |
| 4 | 2.14 | 341 | 1 | 207° C. (FP 90) |
| 5 | 2.76 | 370 | 1 | 161.6° C. (FP 90) |
| 6 | 2.26 | 369 | 4 | 171.1° C. (FP 90) |
| 7 | 2.7 | 333 | 3 | 153.8° C. (FP 90) |
| 8 | 0.86 | 305 | 4 | n.d. |
| 9 | 1.35 | 334 | 4 | 100.5° C. (FP 90) |
| 10 | 2.43 | 399 | 6 | 199° C. (FP 90) |

TABLE 2-continued

Analytical data - $R_t$ means retention time (in minutes), $[M + H]^+$ means the protonated mass of the compound, method refers to the method used for (LC)MS.

| Co. Nr. | $R_t$ | $[M + H]^+$ | Method | Melting Point |
|---|---|---|---|---|
| 11 | 2.43 | 399 | 6 | n.d. |
| 12 | 2.31 | 339 | 4 | 105.3° C. (FP 90) |
| 13 | 3.01 | 399 | 7 | 202.3° C. (FP 90) |
| 14 | 2.41 | 339 | 5 | 55.5° C. (FP 90) |
| 15 | 3.07 | 389 | 5 | 198.6° C. (FP 90) |
| 16 | 1.02 | 323 | 5 | decomposed |
| 17 | 1.8 | 381 | 4 | n.d. |
| 18 | 2.11 | 364 | 4 | 202.9° C. (FP 90) |
| 19 | 2.75 | 387 | 4 | 96.5° C. (FP 90) |
| 20 | 2.88 | 371 | 4 | 112° C. (FP 90) |
| 21 | 3.47 | 402 | 7 | 89.3° C. (FP90) |
| 22 | 2.67 | 402 | 6 | n.d. |
| 23 | 2.66 | 402 | 6 | n.d. |
| 24 | 3.84 | 424 | 7 | 175.2° C. (FP90) |
| 25 | 2.96 | 424 | 6 | n.d. |
| 26 | 2.96 | 424 | 6 | n.d. |
| 27 | 2.94 | 501 | 5 | 198° C. (FP90) |
| 28 | 3.01 | 501 | 6 | n.d. |
| 29 | 3.01 | 501 | 6 | n.d. |
| 30 | 2.62 | 464 | 5 | 218.1° C. (FP90) |
| 31 | 2.82 | 464 | 6 | n.d. |
| 32 | 2.82 | 464 | 6 | n.d. |
| 33 | 2.12 | 443 | 5 | 272.6° C. (FP90) |
| 34 | 1.95 | 422 | 5 | 227.8° C. (FP90) | n.d. means not determined

Optical Rotations:

Optical rotations were measured on a Perkin-Elmer 341 polarimeter with a sodium lamp.

TABLE 3

Analytical data - Optical rotation values for enantiomerically pure compounds

| Co. Nr. | $\alpha_D$ (°) | Wavelength (nm) | Concentration w/v % | Solvent | Temp. (° C.) |
|---|---|---|---|---|---|
| 7 | −42.6 | 589 | 0.54 | DMF | 20 |
| 8 | −48.4 | 589 | 0.5 | MeOH | 20 |
| 9 | −26.2 | 589 | 0.62 | MeOH | 20 |
| 10 | −27.7 | 589 | 0.52 | DMF | 20 |
| 11 | 27.3 | 589 | 0.52 | DMF | 20 |
| 17 | −64.2 | 589 | 0.52 | DMF | 20 |
| 19 | −33.6 | 589 | 0.56 | DMF | 20 |
| 20 | −56.7 | 589 | 0.53 | DMF | 20 |
| 22 | −29.2 | 589 | 0.5 | DMF | 20 |
| 23 | 41.3 | 589 | 0.5 | DMF | 20 |
| 25 | 14.6 | 589 | 0.55 | DMF | 20 |
| 26 | −14.9 | 589 | 0.52 | DMF | 20 |
| 33 | 45.3 | 589 | 0.59 | DMF | 20 |
| 34 | 46.6 | 589 | 0.59 | DMF | 20 |

SFCMS-Methods:

General Procedure for SFC-MS Methods

The SFC measurement was performed using an Analytical SFC system from Berger instruments (Newark, Del., USA) comprising a FCM-1200 dual pump fluid control module for delivering carbon dioxide (CO2) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 μa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

Method 1:

In addition to the general procedure: The chiral separation in SFC was carried out on a CHIRALPAK AD DAICEL column (10 μm, 4.6×250 mm) at 35° C. with a flow rate of 3.0 ml/min. The mobile phase is $CO_2$, 50% Ethanol, 50% EtOH (containing 0.3% iPrNH$_2$) hold 7 min.

Method 2:

In addition to the general procedure A: The chiral separation in SFC was carried out on a CHIRALPAK AD DAICEL column (10 μm, 4.6×250 mm) at 35° C. with a flow rate of 3.0 ml/min. The mobile phase is CO2, 20% Methanol (containing 0.3% iPrNH2) hold 7 min.

Method 3:

In addition to the general procedure A: The chiral separation in SFC was carried out on a CHIRALPAK AD DAICEL column (10 μm, 4.6×250 mm) at 35° C. with a flow rate of 3.0 ml/min. The mobile phase is CO2, 25% Isopropanol (containing 0.3% iPrNH2) hold 7 min.

Method 4:

In addition to the general procedure A: The chiral separation in SFC was carried out on a CHIRALPAK AD DAICEL column (10 μm, 4.6×250 mm) at 35° C. with a flow rate of 3.0 ml/min. The mobile phase is CO2, 30% Ethanol (containing 0.3% iPrNH2) hold 7 min.

TABLE 4

Analytical SFC data - $R_t$ means retention time (in minutes), $[M + H]^+$ means the protonated mass of the compound, method refers to the method used for SFC/MS analysis of enantiomerically pure compounds.

| Co. Nr. | $R_t$ | $[M + H]^+$ | UV Area % | Method | Isomer Elution Order |
|---|---|---|---|---|---|
| 10 | 2.50 | 399 | 100 | 1 | A |
| 11 | 4.27 | 399 | 100 | 1 | B |
| 22 | 2.91 | 402 | 100 | 2 | A |
| 23 | 4.81 | 402 | 100 | 2 | B |
| 25 | 2.73 | 424 | 100 | 3 | A |
| 26 | 3.67 | 424 | 100 | 3 | B |
| 28 | 2.83 | 501 | 100 | 4 | A |
| 29 | 3.83 | 501 | 100 | 4 | B |
| 31 | 2.21 | 464 | 100 | 4 | A |
| 32 | 3.49 | 464 | 100 | 4 | B |

Pharmacological Examples

The compounds provided in the present invention are inhibitors of the β-site APP-cleaving enzyme 1 (BACE1) Inhibition of BACE1, an aspartic protease, is believed to be relevant for treatment of Alzheimer's Disease (AD). The production and accumulation of β-amyloid peptides (Aβ) from the β-amyloid precursor protein (APP) is believed to play a key role in the onset and progression of AD. Aβ is produced from the amyloid precursor protein (APP) by sequential cleavage at the N- and C-termini of the Aβ domain by β-secretase and γ-secretase, respectively.

Compounds of Formula (I) are expected to have their effect substantially at BACE1 by virtue of their ability to inhibit the enzymatic activity. The behaviour of such inhibitors tested using a biochemical Fluorescence Resonance Energy Transfer (FRET) based assay and a cellular alisa assay in SKNBE2 cells described below and which are suitable for the identification of such compounds, and more particularly the compounds according to Formula (I), are shown in Table 1.

Biochemical FRET Based Assay

This assay is a Fluorescence Resonance Energy Transfer Assay (FRET) based assay. The substrate for this assay is an APP derived 13 amino acids peptide that contains the 'Swedish' Lys-Met/Asn-Leu mutation of the amyloid precursor protein (APP) β-secretase cleavage site. This substrate also contains two fluorophores: (7-methoxycoumarin-4-yl) acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by BACE1, the fluorophore Mca is separated from the quenching group Dnp, restoring the full fluorescence yield of the donor. The increase in fluorescence is linearly related to the rate of proteolysis (Koike H et al. J Biochem. 1999, 126, 235-42). Briefly in a 384-well format recombinant BACE1 protein in a final concentration of 1 μg/ml is incubated for 120 minutes at room temperature with 10 μm substrate in incubation buffer (40 mM Citrate buffer pH 5.0, 0.04% PEG, 4% DMSO) in the absence or presence of compound. Next the amount of proteolysis is directly measured by fluorescence measurement at T=0 and T=120 (excitation at 320 nm and emission at 405 nm). Results are expressed in RFU, as difference between T120 and T0 A best-fit curve is fitted by a minimum sum of squares method to the plot of % Controlmin versus compound concentration. From this an IC50 value (inhibitory concentration causing 50% inhibition of activity) can be obtained.

$LC$ = Median of the low control values

= Low control: Reaction without enzyme $HC$ = Median of the High control values

= High Control: Reaction with enzyme

% Effect = $100 - [(sample-LC)/(HC-LC)*100]$

% Control = $(sample/HC)*100$

% Controlmin = $(sample-LC)/(HC-LC)*100$

The following exemplified compounds were tested essentially as described above and exhibited the following the activity:

TABLE 5

| Co. Nr. | Biochemical FRET based assay pIC$_{50}$ |
|---|---|
| 1 | 5.48 |
| 2 | 5.78 |
| 3 | 6.87 |
| 4 | 5.06 |
| 5 | 5.49 |
| 6 | 5.53 |
| 7 | 6.12 |
| 8 | 5.65 |
| 9 | 6.05 |
| 10 | <4.52 |
| 11 | 7.37 |
| 12 | 4.88 |
| 13 | 6.84 |
| 14 | 6.11 |
| 15 | 5.68 |
| 16 | 4.98 |

TABLE 5-continued

| Co. Nr. | Biochemical FRET based assay pIC$_{50}$ |
|---|---|
| 17 | 7.31 |
| 18 | 4.75 |
| 19 | 5.77 |
| 20 | 6.76 |
| 21 | 5.97 |
| 22 | 6.22 |
| 23 | <4.52 |
| 24 | 5.14 |
| 25 | 5.44 |
| 26 | <4.52 |
| 27 | 6.84 |
| 28 | 7.04 |
| 29 | 4.81 |
| 30 | 6.68 |
| 31 | 6.73 |
| 32 | <4.52 |
| 33 | 6.51 |
| 34 | 6.51 |

Cellular αlisa Assay in SKNBE2 Cells

In two αlisa assays the levels of Aβtotal and Aβ42 produced and secreted into the medium of human neuroblastoma SKNBE2 cells are quantified. The assay is based on the human neuroblastoma SKNBE2 expressing the wild type Amyloid Precursor Protein (hAPP695). The compounds are diluted and added to these cells, incubated for 18 hours and then measurements of Aβ42 and Aβtotal are taken. Aβtotal and Aβ42 are measured by sandwich αlisa. αlisa is a sandwich assay using biotinylated antibody AbN/25 attached to streptavidin coated beads and antibody Ab4G8 or cAb42/26 conjugated acceptor beads for the detection of Aβtotal and Aβ42 respectively. In the presence of Aβtotal or Aβ42, the beads come into close proximity. The excitation of the Donor beads provokes the release of singlet oxygen molecules that triggers a cascade of energy transfer in the Acceptor beads, resulting in light emission. Light emission is measured after 1 hour incubation (excitation at 650 nm and emission at 615 nm).

A best-fit curve is fitted by a minimum sum of squares method to the plot of % Controlmin versus compound concentration. From this an IC50 value (inhibitory concentration causing 50% inhibition of activity) can be obtained.

LC = Median of the low control values
  = Low control: cells preincubated without compound, without biotinylated Ab in the αlisa HC = Median of the High control values
  = High Control: cells preincubated without compound % Effect = 100 − [(sample-LC)/(HC-LC) * 100]
% Control = (sample/HC) * 100
% Controlmin = (sample-LC)/(HC-LC) * 100

The following exemplified compounds were tested essentially as described above and exhibited the following the activity:

TABLE 6

| Co. Nr. | Cellular αlisa assay in SKNBE2 cells Aβ42 pIC$_{50}$ | Cellular αlisa assay in SKNBE2 cells Aβtotal pIC$_{50}$ |
|---|---|---|
| 1 | 6.34 | 6.45 |
| 2 | 6.95 | 6.98 |
| 3 | 7.97 | 7.93 |
| 4 | 5.97 | 5.98 |
| 5 | 6.4 | 6.41 |
| 6 | 6.06 | 6.13 |
| 7 | 6.56 | 6.58 |
| 8 | 6.61 | 6.54 |
| 9 | 6.93 | 6.94 |
| 10 | 5.41 | 5.44 |
| 11 | 8.36 | 8.37 |
| 12 | 5.58 | 5.67 |
| 13 | 7.72 | 7.73 |
| 14 | 6.09 | 6.11 |
| 15 | 5.48 | 5.52 |
| 16 | 5.53 | 5.48 |
| 17 | 8.09 | 8.08 |
| 18 | 5.76 | 5.67 |
| 19 | 5.81 | 5.91 |
| 20 | 6.33 | 6.37 |
| 21 | 6.39 | 6.4 |
| 22 | 6.13 | 6.18 |
| 23 | <5 | <5 |
| 24 | 5.23 | 5.27 |
| 25 | 5.5 | 5.64 |
| 26 | <5 | <5 |
| 27 | 6.77 | 6.77 |
| 28 | 6.99 | 7.1 |
| 29 | <5 | <5 |
| 30 | 6.8 | 6.78 |
| 31 | 6.92 | 6.99 |
| 32 | 6.56 | 6.54 |
| 33 | 7.59 | 7.68 |
| 34 | 7.11 | 7.19 | n.t. means not tested

Demonstration of In Vivo Efficacy

Aβ peptide lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ peptide lowering agents can be administered in any standard form using any standard method. For example, but not limited to, Aβ peptide lowering agents can be in the form of liquid, tablets or capsules that are taken orally or by injection. Aβ peptide lowering agents can be administered at any dose that is sufficient to significantly reduce levels of Aβ peptides in the blood, blood plasma, serum, cerebrospinal fluid (CSF), or brain.

To determine whether acute administration of an Aβ42 peptide lowering agent would reduce Aβ peptide levels in vivo, non-transgenic rodents, e.g. mice or rats were used. Animals treated with the Aβ peptide lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ peptide lowering compounds were formulated in 20% hydroxypropyl β cyclodextrin. The Aβ peptide lowering agents were administered as a single oral dose (p.o.) or a single subcutaneous dose (s.c.) to overnight fasted animals. After a certain time, usually 2 or 4 h (as indicated in Table 19), the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 µl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Ill.). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model at least 20% Aβ42 lowering compared to untreated animals would be advantageous.

The following exemplified compounds were tested essentially as described above and exhibited the following activity:

TABLE 20

| Co. No. | Aβ42 (% Ctrl)_Mean | Aβtotal (% Ctrl)_Mean | Dose | Route of administration | Time after administration |
|---|---|---|---|---|---|
| 2 | 109 | 116 | 30 mpk | sc | 4 h |
| 11 | 71 | 80 | 30 mpk | sc | 4 h |
| 20 | 86 | 80 | 30 mpk | sc | 2 h | s.c. means subcutaneous; p.o. means oral

The invention claimed is:
1. A compound of Formula (I)

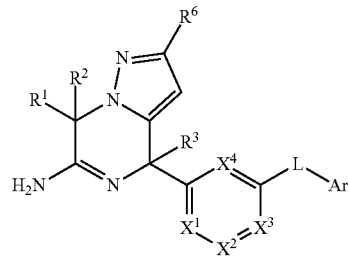

or a tautomer or a stereoisomeric form thereof, wherein
$R^1$ and $R^2$ are independently selected from the group consisting of hydrogen, fluoro, cyano, $C_{1-3}$alkyl, mono- and polyhalo-$C_{1-3}$alkyl, and $C_{3-6}$cycloalkyl; or
$R^1$ and $R^2$ taken together with the carbon atom to which they are attached may form a $C_{3-6}$cycloalkanediyl ring;
$R^3$ is selected from the group consisting of hydrogen, $C_{1-3}$alkyl, $C_{3-6}$cycloalkyl, mono- and polyhalo-$C_{1-3}$alkyl, homoaryl and heteroaryl;
$X^1, X^2, X^3, X^4$ are independently $C(R^4)$ or N, provided that no more than two thereof represent N; each $R^4$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;
L is a bond or —N($R^5$)CO—, wherein $R^5$ is hydrogen or $C_{1-3}$alkyl;
$R^6$ is hydrogen or trifluoromethyl;
Ar is homoaryl or heteroaryl;
homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl; and mono- and polyhalo-$C_{1-3}$alkyloxy;
heteroaryl is selected from the group consisting of pyridyl, pyrimidyl, pyrazyl, pyridazyl, furanyl, thienyl, pyrrolyl, pyrazolyl, imidazolyl, triazolyl, thiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl; and mono- and polyhalo-$C_{1-3}$alkyloxy; or an addition salt thereof.

2. The compound of claim 1 wherein,
$R^1$ and $R^2$ are independently selected from hydrogen and $C_{1-3}$alkyl;
$X^1, X^2, X^3, X^4$ are independently $C(R^4)$ wherein each $R^4$ is selected from hydrogen and halo;
L is a bond or —N($R^5$)CO—, wherein $R^5$ is hydrogen;
Ar is homoaryl or heteroaryl;
homoaryl is phenyl or phenyl substituted with one or two substituents selected from the group consisting of halo, cyano, $C_{1-3}$alkyl, and $C_{1-3}$alkyloxy;

heteroaryl is selected from the group consisting of pyridyl, pyrimidyl, and pyrazyl, each optionally substituted with one or two substituents selected from the group consisting of halo, cyano, $C_{1-3}$alkyl, and $C_{1-3}$alkyloxy; or an addition salt thereof.

3. The compound of claim 1 wherein, $R^1$ and $R^2$ are hydrogen;

$X^2$, $X^3$, $X^4$ are CH;

L is a bond or —N($R^5$)CO—, wherein $R^5$ is hydrogen;

Ar is homoaryl or heteroaryl;

homoaryl is phenyl substituted with chloro;

heteroaryl is selected from the group consisting of pyridyl and pyrimidyl, each optionally substituted with one or two substituents selected from the group consisting of chloro, fluoro, cyano, methyl, and methoxy; or an addition salt thereof.

4. The compound of claim 1 wherein the carbon atom substituted with $R^3$ has the R-configuration.

5. A pharmaceutical composition comprising a therapeutically effective amount of a compound as defined in claim 1 and a pharmaceutically acceptable carrier.

6. A pharmaceutical composition comprising a therapeutically effective amount of a compound as defined in claim 4 and a pharmaceutically acceptable carrier.

7. A method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, comprising administering to a subject in need thereof, a therapeutically effective amount of a compound as defined in claim 1.

\* \* \* \* \*

UNITED STATES PATENT AND TRADEMARK OFFICE
CERTIFICATE OF CORRECTION

| | | |
|---|---|---|
| PATENT NO. | : 8,609,660 B2 | Page 1 of 1 |
| APPLICATION NO. | : 13/825139 | |
| DATED | : December 17, 2013 | |
| INVENTOR(S) | : Andrés Avelino Trabanco-Suárez, Gary John Tresadern and Francisca Delgado-Jiménez | |

It is certified that error appears in the above-identified patent and that said Letters Patent is hereby corrected as shown below:

In the Claims:
Column 81, line 8, claim 3, please insert -- $X^1$, -- the beginning of the line.

Signed and Sealed this
Twenty-ninth Day of July, 2014

Michelle K. Lee
*Deputy Director of the United States Patent and Trademark Office*